US009605060B2

(12) United States Patent
Walker et al.

(10) Patent No.: US 9,605,060 B2
(45) Date of Patent: Mar. 28, 2017

(54) MULTIPLEX IMMUNOASSAYS FOR HEMOGLOBIN, HEMOGLOBIN VARIANTS, AND GLYCATED FORMS

(71) Applicant: Bio-Rad Laboratories, Inc., Hercules, CA (US)

(72) Inventors: Roger Walker, Benicia, CA (US); Benedicte Jardin, Saint Clement de Riviere (FR)

(73) Assignee: BIO-RAD LABORATORIES, INC., Hercules, CA (US)

(*) Notice: Subject to any disclaimer, the term of this patent is extended or adjusted under 35 U.S.C. 154(b) by 0 days.

(21) Appl. No.: 14/947,939

(22) Filed: Nov. 20, 2015

(65) Prior Publication Data

US 2016/0068594 A1 Mar. 10, 2016

Related U.S. Application Data

(60) Division of application No. 14/081,799, filed on Nov. 15, 2013, now Pat. No. 9,213,034, which is a (Continued)

(51) Int. Cl.

| | |
|---|---|
| ***C07K 16/18*** | (2006.01) |
| ***G01N 33/531*** | (2006.01) |

(Continued)

(52) U.S. Cl.

CPC ........... *C07K 16/18* (2013.01); *G01N 33/531* (2013.01); *G01N 33/582* (2013.01); (Continued)

(58) Field of Classification Search

CPC .. G01N 33/582; G01N 33/721; G01N 33/723; G01N 33/531; C07K 16/18; (Continued)

(56) References Cited

U.S. PATENT DOCUMENTS

| | | | |
|---|---|---|---|
| 4,752,583 | A | 6/1988 | Jensen et al. |
| 5,478,754 | A | 12/1995 | Brandt et al. |

(Continued)

FOREIGN PATENT DOCUMENTS

| | | |
|---|---|---|
| WO | 02088185 | 11/2002 |
| WO | 2004096009 A2 | 11/2004 |

(Continued)

OTHER PUBLICATIONS

Campbell, et al., "Detection of hemoglobin variants in erythrocytes by flow cytometry," *Cytometry*, vol. 35, pp. 242-248 (1999).

(Continued)

*Primary Examiner* — Gail R Gabel

(74) *Attorney, Agent, or Firm* — Kilpatrick Townsend & Stockton LLP

(57) ABSTRACT

Hemoglobin, its variants, and glycated forms of each are determined individually in a multiplex assay that permits correction of the measured level of HbA1c to account for glycated variants and other factors related to the inclusion of the variants in the sample. New antibodies that are particularly well adapted to the multiplex assay are also provided.

3 Claims, 2 Drawing Sheets

Related U.S. Application Data continuation of application No. 12/941,738, filed on Nov. 8, 2010, now Pat. No. 8,603,828.

(60) Provisional application No. 61/262,488, filed on Nov. 18, 2009.

(51) Int. Cl.
*G01N 33/58* (2006.01)
*G01N 33/72* (2006.01)

(52) U.S. Cl.
CPC ......... *G01N 33/721* (2013.01); *G01N 33/723* (2013.01); *C07K 2317/34* (2013.01); *C07K 2317/92* (2013.01); *Y10T 436/101666* (2015.01); *Y10T 436/25125* (2015.01)

(58) Field of Classification Search
CPC ............ C07K 2317/92; C07K 2317/34; Y10T 436/101666; Y10T 436/25125
See application file for complete search history.

(56) References Cited

U.S. PATENT DOCUMENTS

| | | | | |
|---|---|---|---|---|
| 6,043,043 | A | 3/2000 | Yip | |
| 6,280,618 | B2 | 8/2001 | Watkins et al. | |
| 6,872,578 | B2 | 3/2005 | Watkins et al. | |
| 6,913,935 | B1 | 7/2005 | Thomas | |
| 6,933,106 | B2 | 8/2005 | Hechinger | |
| 6,951,716 | B2 | 10/2005 | Hechinger | |
| 7,271,009 | B1 | 9/2007 | Watkins et al. | |
| 7,326,573 | B2 | 2/2008 | Bell | |
| 7,521,244 | B2 | 4/2009 | Rannikko et al. | |
| 8,603,828 | B2 | 12/2013 | Walker et al. | |
| 8,658,396 | B2 * | 2/2014 | Turner | 435/69.6 |
| 9,213,034 | B2 | 12/2015 | Walker et al. | |
| 2002/0115116 | A1 | 8/2002 | Song et al. | |
| 2004/0101874 | A1 * | 5/2004 | Ghosh | G01N 33/5079 435/6.12 |
| 2004/0214243 | A1 | 10/2004 | Burshteyn et al. | |
| 2004/0229284 | A1 | 11/2004 | Luciw et al. | |
| 2005/0158866 | A1 | 7/2005 | Xie et al. | |

FOREIGN PATENT DOCUMENTS

| | | | |
|---|---|---|---|
| WO | 2009/067421 | A1 | 5/2009 |
| WO | 2010/021914 | A2 | 2/2010 |

OTHER PUBLICATIONS

Delahunty, "Convenient Screening for Hemoglobin Variants by Using the Diamat HPLC System," *Clin Chem.*, vol. 36(6), pp. 903-905 (1990).

Elbaggari, et al., "Evaluation of the Criterion Stain Free™ Gel Imaging System for Use in Western Blotting Application," *Bio-Rad Laboratories, Inc. Bulletin*, 5861 Rev. A., 4 pages, (2008).

Papayannopoulou, et al., "Use of Specific Fluorescent Antibodies for the Identification of Hemoglobin C in Erthrocytes," *Am. J Hematol.*, vol. 2(2), pp. 105-112 (1977).

Epstein, et al., "Monoclonal antibody-based methods for quantitation of hemoglobins: application to evaluating patients with sickle cell anemia treated with hydroxyurea," *Eur. J. Haemotol.*, vol. 57(1), pp. 17-24 (1996).

Garver, et al., "Screening for hemoglobins S and C in newborn and adult blood with a monoclonal antibody in an ELISA procedure," *Annals of Hematology*, vol. 60(6), pp. 334-338 (1990).

Jensen, et al., "Monoclonal antibodies specific for sickle cell hemoglobin," *Hemoglobin*, vol. 9(4), pp. 349-362 (1985).

Moscoso, et al., "Enzyme immunoassay for the identification of hemoglobin variants," *Hemoglobin*, vol. 14(4), pp. 389-398 (1990).

Rosenthal, et al., "Binding specificity of a monoclonal antibody to human HbA," *Hemoglobin*, vol. 19(3-4), pp. 191-196 (1995).

Schultz, "Utilization of Monoclonal-Antibody-Based Assay (HemoCard™) in Screening for and Differentiating Between Genotypes of Sickle Cell Disease and Other Hemoglobinopathies," *J. Clin. Lab. Anal.*, vol. 9(6), pp. 366-374 (1995).

Stanker, et al., "Monoclonal antibodies recognizing single amino acid substitutions in hemoglobin," *J. Immunol.*, vol. 136(11), pp. 4174-4180 (1986).

International Search Report and Written Opinion for PCT/US10/55952, 18 pages, mailed May 25, 2011.

Supplementary European Search Report from EP 0832004.5, dated Feb. 27, 2013 (13 pages).

"Hemoglobin D Disease", Department of pediatric hematology, Primary children's medical center, Salt Lake city, Utah USA, Fact sheets for health care providers, Utah department of health, Aug. 1, 2008, pp. 1-2.

Rosenthal et al., "Monoclonal antibody immunoassay for the identification of hemoglobin variants in neonatal screening", Screening, vol. 3, Issue 2, Jan. 1, 1994, pp. 67-76.

EP16155015.7 , "Extended European Search Report", Mar. 29, 2016, 11 pages.

* cited by examiner

MULTIPLEX IMMUNOASSAYS FOR HEMOGLOBIN, HEMOGLOBIN VARIANTS, AND GLYCATED FORMS

CROSS-REFERENCE TO RELATED APPLICATION

This application is a divisional application of U.S. application Ser. No. 14/081,799 filed Nov. 15, 2013, issued Dec. 15, 2015 as U.S. Pat. No. 9,213,034, which is a continuation application of U.S. application Ser. No. 12/941,738 filed Nov. 8, 2010, issued Dec. 10, 2013 as U.S. Pat. No. 8,603,828, which claims the benefit of U.S. Provisional Patent Application No. 61/262,488 filed Nov. 18, 2009, each of which applications is herein incorporated by reference.

REFERENCE TO A SEQUENCE LISTING SUBMITTED AS AN ASCII TEXT FILE

The Sequence Listing written in file SEQTXT_95191-087430US-0963968.TXT, created on Nov. 6, 2015 and containing 16,000 bytes, machine format IBM-PC, MS-Windows operating system is hereby incorporated by reference.

BACKGROUND OF THE INVENTION

1. Field of the Invention

This invention lies in the field of assays for glycated hemoglobin.

2. Description of the Prior Art

For individuals suffering from type 1 or type 2 diabetes mellitus, maintenance of glycemic control is of prime importance, and such maintenance requires the determination of the level of hemoglobin $A_{1c}$ in the blood of these individuals. With diabetes reaching global epidemic proportions, it is particularly important to have accurate and reproducible $HbA_{1c}$ assays. $HbA_{1c}$ assays are also used in the screening of individuals for diabetes.

$HbA_{1c}$ measurements for both patient monitoring and screening are taken as an average over the lifetime of an erythrocyte. This average is compromised by several physiological conditions, notable among which are the presence of hemoglobin variants and thalassemias in the patient's blood. Hemoglobin variants are prevalent among certain ethnic groups and in certain geographical regions. Of the over 800 variants known worldwide, the most common are HbS, HbC, HbD, and HbE. HbS is most prevalent among individuals of African descent, HbD among individuals of Punjabi Indian descent, and HbE among individuals of Southeast Asia. Other known forms of hemoglobin are HbF (fetal hemoglobin) and HbA2, both of which can be elevated in thalassemia, a relatively common condition characterized by an imbalance of hemoglobin alpha and beta subunits. Beta thalassemias can also occur in the presence of HbE and HbS, and the combined sickle/beta thalassemia trait occurs most frequently among individuals of Mediterranean descent. Variants and thalassemias can cause inaccuracies in $HbA_{1c}$ measurements by affecting such factors as red blood cell survival and glycosylation rates. Variants also affect immunologically determined levels of glycated hemoglobin since immunoreactivity differs from one glycated variant to the next and also between glycated variants and HbA itself. Health care professionals must therefore know of the presence of variants and their proportions relative to HbA as well as the presence of thalassemias to achieve a proper determination of glycemic control.

Determinations of hemoglobin variants are typically done separately from determinations of $HbA_{1c}$ regardless of whether a variant is actually known to be present. Antibodies to specific variants have been developed for this purpose, and the following is a sampling of reports on such antibodies:

HbS: Jensen, R. H., et al., "Monoclonal antibodies specific for sickle cell hemoglobin," *Hemoglobin* 9(4), 349-362 (1985)

HbS: Epstein, N., et al., "Monoclonal antibody-based methods for quantitation of hemoglobins: application to evaluating patients with sickle cell anemia treated with hydroxyurea," *Eur. J. Haemotol.* 57(1), 17-24 (1996)

HbA: Rosenthal, M. A., et al., "Binding specificity of a monoclonal antibody to human HbA," *Hemoglobin* 19(3-4), 191-196 (1995)

HbS and HbC: Garver, E. A., et al., "Screening for hemoglobins S and C in newborn and adult blood with a monoclonal antibody in an ELISA procedure," *Annals of Hematology* 60(6), 334-338 (1990)

Hb with single amino acid substitutions: Stanker, L. H., et al., "Monoclonal antibodies recognizing single amino acid substitutions in hemoglobin," *J. Immunol.* 136 (11), 4174-4180 (1986)

Hb variants: Moscoso. H., et al., "Enzyme immunoassay for the identification of hemoglobin variants," *Hemoglobin* 14(4), 389-98 (1990)

Hb variants: Schultz, J. C., "Utilization of monoclonal antibody-based assay HemoCard in screening for and differentiating between genotypes of sickle cell disease and other hemoglobinopathies," *J. Clin. Lab. Anal.* 9(6), 366-374 (1995)

Despite these reports and others, determinations of variants are presently performed by either high performance liquid chromatography (HPLC) or electrophoresis. HPLC can indeed be a rapid means of obtaining the $HbA_{1c}$ level, but extended HPLC gradients are needed for detecting and quantifying the variants and thalassemias, since in HPLC impurities co-elute with the variants, and different variants tend to co-elute with each other. In fact, certain variants cannot be resolved by HPLC, even with the most optimized HPLC gradients. Typically, separate HPLC methods for rapid $A_{1c}$ measurements and variant and thalassemia testing are used, therefore making it impossible to simultaneously determine the $A_{1c}$ level and variant or thalassemia status by HPLC, much less in a rapid manner.

Assays that provide simultaneous detection of multiple analytes are termed "multiplex" assays, and disclosures of multiplex assays using affinity-type binding reactions on the surfaces of beads that are then detected by flow cytometry are disclosed in the following patents:

Watkins, M. I., et al., "Magnetic particles as solid phase for multiplex flow assays," U.S. Pat. No. 6,280,618 B2, issued Aug. 28, 2001

Watkins, M. I., et al., "Magnetic particles as solid phase for multiplex flow assays," U.S. Pat. No. 6,872,578 B2, issued Mar. 29, 2005

Thomas, N., "Multiple assay method," U.S. Pat. No. 6,913,935 B1, issued Jul. 5, 2005

Hechinger, M., "Platelet immunoglobulin bead suspension and flow cytometry," U.S. Pat. No. 6,933,106 B1, issued Aug. 23, 2005

Hechinger, M., "Anti-platelet immunoglobulin bead positive control," U.S. Pat. No. 6,951,716 B1, issued Oct. 4, 2005

Watkins, M. I., et al., "Multi-analyte diagnostic test for thyroid disorders," U.S. Pat. No. 7,271,009 B1, issued Sep. 8, 2007

Bell, M. L., "Assay procedures and apparatus," U.S. Pat. No. 7,326,573 B2, issued Feb. 5, 2008

Song, Y., et al., "Multiplex protein interaction determinations using glutathione-GST binding," US 2002/0115116 A1, published Aug. 22, 2002

The success of multiplex assays for certain combinations of analytes does not however provide assurance, or even a high level of expectation, that similar success will be achieved for all combinations of analytes, particularly combinations with a high level of homology among the analytes. Hemoglobin and its variants and glycated forms are one such combination. Multiplex assays involve a plurality of different immunoreactants in intimate mixture in a common reaction medium, which creates competition among the immunoreactants for the different analytes, more so than in media where a single immunoreactant is present, and the cross-reactivities occur in multiple directions. The bead sets themselves must also be differentiated at the same time as the immunoassays are performed. This differentiation, whether by the use of different dyes on different bead sets, a different size for each bead set, or other known differentiation factors, adds a further level of complexity and further opportunities for cross-talk.

SUMMARY OF THE INVENTION

The present invention resides in the discovery that hemoglobin variants can be differentiated from each other and from $HbA_{1c}$ and from total hemoglobin, and the levels of each measured, in a multiplex immunoassay. The assay can, e.g., detect a single variant in addition to $HbA_{1c}$ and total hemoglobin or two or more variants and total hemoglobin. When two or more variants are detected, different combinations of variants can be selected, although preferably the assay will include the four most common variants, HbS, HbC, HbE, and HbD. The assay may also include the measurement of $HbA_2$ and HbF. The invention thus resides in a method for detecting and identifying the presence of hemoglobin variants in a patient's blood. The invention also resides in a method for measuring the level of HbA1c relative to total hemoglobin while correcting the result for the presence of variants that may also be present. Here as well, the correction can be for individual variants or combinations of variants. The invention also resides in a method for the simultaneous detection of $A_{1c}$ and hemoglobin variants without correction, which is useful in certain cases. A still further aspect of the invention is the measurement of levels of particular variants in glycated form. When a variant is known to be present, the glycated version of that variant can be measured and added to the level of $HbA_{1c}$ to obtain an accurate indication of total glycated hemoglobin.

In a further aspect, the invention provides antibodies having selective binding affinity for hemoglobin variants that can be used in the methods of the invention. In some embodiments, the invention provides a monoclonal antibody that has selective binding affinity for HbC and glycated HbC, wherein the monoclonal antibody binds to an HbC minimal epitope $^{4}$TPKEKSAVT$^{12}$ (SEQ ID NO:1); or to an HbC minimal epitope comprising the amino acid sequence $TX_1KE$ or $LTX_1KE$ (SEQ ID NO:2), wherein $X_1$ is one of the 20 common naturally occurring amino acids. In some embodiments, the invention provides a monoclonal antibody having selective binding affinity for HbS and glycated HbS, wherein the monoclonal antibody binds to an HbS minimal epitope $^{3}$LTPVEKSAVT$^{12}$ (SEQ ID NO:3); or to an HbS minimal epitope comprising the amino acid sequence $PVEX_2X_3A$ (SEQ ID NO:4) or $LTPVEX_2X_3A$ (SEQ ID NO:5), wherein each of $X_2$ and $X_3$ is an amino acid independently selected from the 20 common naturally occurring amino acids. In some embodiments, the invention provides a monoclonal antibody having selective binding affinity for HbE and glycated HbE, wherein the antibody binds to an HbE minimal epitope $^{22}$EVGGK$^{26}$ (SEQ ID NO:6); or to an HbE minimal epitope comprising the amino acid sequence DEVGGK (SEQ ID NO:7) or $EVX_4X_5K$, wherein each of $X_4$ and $X_5$ is an amino acid independently selected from the 20 common naturally occurring amino acids. In some embodiments, the invention provides a monoclonal antibody having selective binding affinity for HbD and glycated HbD, where the monoclonal antibody binds to an HbD minimal epitope $^{121}$QFTPP$^{125}$ (SEQ ID NO:8); or to an HbD minimal epitope comprising the amino acid sequence $GX_6QFX_7PP$ (SEQ ID NO:9) or $QFX_7PP$ (SEQ ID NO:10), wherein each of $X_6$ and $X_7$ is an amino acid independently selected from the 20 common naturally occurring amino acids.

The invention also may employ an antibody, either a polyclonal antibody or monoclonal antibody that selectively binds total hemoglobin (in comparison to non-hemoglobin polypeptides). In some embodiments, a pan-reactive polyclonal antibody for use in the invention binds to one or more epitopes present in the following regions of alpha globin and beta globin: alpha globin $^{49}$SHGSAQVKGHGKKVADALT-NAVAHVDDMPNALSALSDHLHA HKLRRVDPV$^{96}$ (SEQ ID NO:11); beta globin $^{15}$WGKVNVDEVG-GEALG$^{30}$ (SEQ ID NO:12), $^{45}$FGDLSTP$^{51}$ (SEQ ID NO:13), and $^{76}$AHLDNLKGTFAT$^{87}$ (SEQ ID NO:14). In some embodiments, a pan reactive antibody is a monoclonal or polyclonal antibody that binds to the epitope $^{9}$SAVTAL-WGKVNV$^{20}$ (SEQ ID NO:15) (beta globin) or $^{8}$KSAVTAL-WGKVNV$^{20}$ (SEQ ID NO:16) or $^{11}$VTALW$^{15}$ (SEQ ID NO:17) or to a beta globin minimal epitope that comprises the sequence ALWG (SEQ ID NO:18) or $VTX_9LW$ (SEQ ID NO:19), wherein $X_9$ is one of the 20 common naturally occurring amino acids. An antibody for use in the invention may bind to an epitope on beta globin, e.g. $^{8}$KSAVTAL-WGKVNV$^{20}$ (SEQ ID NO:16), $^{58}$PKVKAHGKKVLGAF$^{71}$ (SEQ ID NO:20) or $^{87}$TLSELHCDKLHVDPENFR$^{104}$ (SEQ ID NO:21) (beta globin).

The invention further provides monoclonal antibodies that selectively bind to glycated forms of hemoglobin, including binding to both normal and variant hemoglobins, but do not bind to non-glycated forms of hemoglobin. A glycosylated residue $^{1}$V and residue $^{2}$H are typically important for binding for such antibodies.

The method of the invention may additionally comprise detecting other hemoglobin variants using antibodies, e.g., monoclonal antibodies, that selectively bind such variants.

In typical embodiments, an antibody for use in the invention has a $K_D$ that is anywhere in the range of from about $10^{-6}$ M to about $10^{-12}$ M. In some embodiments, the antibody has a $K_D$ that is anywhere in the range of from about $10^{-7}$ M to about $10^{-11}$ M. In other embodiments, the antibody has a $K_D$ anywhere in the range of about $10^{-8}$ M to about $10^{-10}$ M. Typically the $K_D$ is in the nM range, e.g., anywhere from about $10^{-9}$ M to about $10^{-10}$ M.

These and other features, objects, and advantages of the invention will be better understood from the description that follows.

DETAILED DESCRIPTION OF THE INVENTION AND PREFERRED EMBODIMENTS

Figure 1:
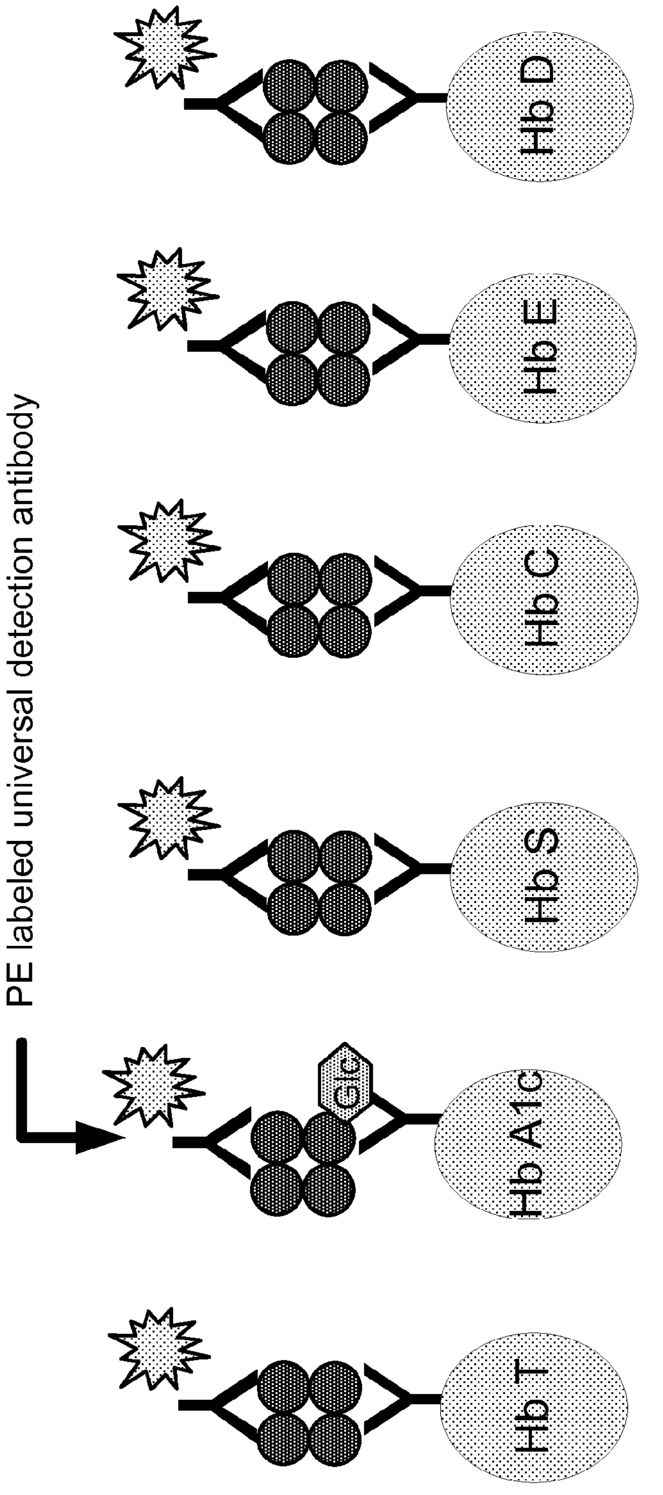
FIG. 1 provides a schematic depicting an example of a sandwich immunoassay for measuring glycated hemoglobin and hemoglobin variants.

The hemoglobin variants to be detected by the present invention are any of the known variants reported in the literature or otherwise known to clinicians and researchers skilled in technology of hemoglobin, glycated hemoglobin, and diabetes. As noted above, the four most common hemoglobin variants are HbS, HbC, HbE, and HbD, although other variants can be detected in addition to these four or in place of one or more of them. For example, two variants that are elevated in beta thalassemia are HbF and $HbA_2$. The binding members used for each of these variants in the multiplex assay are generally monoclonal antibodies, preferably those that are developed expressly for the multiplex assay. The antibodies preferably bind to epitopes on the variants that distinguish each variant from the other variants to minimize cross-reactivity, and most importantly that distinguish the variants from the wild-type hemoglobin A0. In embodiments of the invention requiring the use of a value for the concentration of total hemoglobin in the sample, the concentration can be determined either by an immunoassay method or a non-immunoassay method. An example of a non-immunoassay method is the determination of optical density. Other examples will be readily apparent to those skilled in the hemoglobin art. In embodiments where total hemoglobin is determined by immunoassay, the determination can be performed as part of the multiplex assay. The antibody for total hemoglobin in the multiplex assay can be either a monoclonal antibody or a polyclonal antibody, and the antibody for $HbA_{1c}$ can be either a polyclonal antibody or a monoclonal antibody, preferably a monoclonal antibody.

Antibodies

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term antibody as used herein includes antibody fragments that retain binding specificity. For example, there are a number of well characterized antibody fragments. Thus, for example, pepsin digests an antibody C-terminal to the disulfide linkages in the hinge region to produce F(ab)'2, a dimer of Fab which itself is a light chain joined to VH-CH1 (Fd) by a disulfide bond. The F(ab)'2 may be reduced under mild conditions to break the disulfide linkage in the hinge region thereby converting the (Fab')2 dimer into an Fab' monomer. The Fab' monomer is essentially a Fab with all or part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term "antibody" also includes antibody fragments produced either by the modification of whole antibodies or synthesized using recombinant DNA methodologies. Antibodies include dimers such as $V_H$-$V_L$ dimers, $V_H$ dimers, or $V_L$ dimers, including single chain antibodies. Alternatively, the antibody can be another fragment, such as a disulfide-stabilized Fv (dsFv). Other fragments can also be generated using known techniques, including using recombinant techniques. In some embodiments, antibodies include those that have been displayed on phage or generated by recombinant technology using vectors where the chains are secreted as soluble proteins, e.g., scFv, Fv, Fab, (Fab')2 or generated by recombinant technology using vectors where the chains are secreted as soluble proteins.

As used here, an "immunological binding member having selective binding affinity" for an antigen, e.g., a hemoglobin variant, is typically an antibody. In some embodiments, a binding member having selective binding affinity for an antigen may be a peptide, e.g., that can be identified by screening peptide libraries, that has a selective binding interaction with the antigen.

In one aspect, the invention provides monoclonal antibodies that bind to Hb $A_{1c}$ as well as monoclonal antibodies that specifically bind to hemoglobin variants HbS, HbC, HbE, and HbD. The sequence of hemoglobin beta chain is as follows (SEQ ID NO:22):

```
VHLTPEEKSAVTALWGKVNVDEVGGEALGRLLVVYPWTQRFFESFGDLS

TPDAVMGNPKVKAHGKKVLGAFSDGLAHLDNLKGTFATLSELHCDKLHV

DPENFRLLGNVLVCVLAHHFGKEFTPPVQAAYQKVVAGVANALAHKYH
```

The positions of amino acid residues in the hemoglobin beta chain referred to herein is with reference to this amino acid sequence unless otherwise specified.

Hb $A_{1c}$ is glycated at the N-terminal valine. The most prevalent beta-chain point mutations are HbS (Glu 6→Val); HbC (Glu 6→Lys); HbE (Glu 26→Lys) and HbD (Glu 121→Gln). The Glu 6, Glu 26, and Glu 121 positions are indicated in the beta chain sequence by underline.

$HbA_2$ and HbF can also be determined in the assay of the present invention. Hemoglobin $A_2$ has two alpha chains and two delta chains; and hemoglobin F has two alpha and two gamma chains.

In the context of this invention, the term "specifically binds" or "specifically (or selectively) immunoreactive with," or "having a selective affinity for" refers to a binding reaction where the antibody binds to the antigen of interest. In the context of this invention, the antibody binds to the antigen of interest, e.g., HbS, including the glycated form of HbS, with an affinity that is at least 100-fold better than its affinity for other antigens, e.g., other hemoglobin variants such as $HbA_0$ or HbC.

"Reactivity" as used herein refers to the relative binding signal from the reactions of an antibody with the antigen to which it specifically binds versus other antigens, such as other hemoglobin variants and or wild-type $HbA_0$. Reactivity is assessed using appropriate buffers that permit the antigen and antibody to bind. Reactivity can be determined, e.g., using a direct or sandwich ELISA assay. For example, a direct format assay for determining reactivity with wild-type hemoglobin and/or hemoglobin variants, can be used in which the antigen is directly bound to the ELISA plate, and the various antibodies are added to see which ones bind, followed by interrogation using a labeled anti-mouse antibody such as a phycoerythrin-labeled antibody. In the sandwich format, the monoclonal antibody is bound to the bead, followed by addition of antigen, followed by interrogation with phycoerythrin-labeled universal detection antibody, e.g., a phycoerythrin-labeled universal detection antibody, that binds all hemoglobin species. Thus, in an example using the sandwich format, reactivity can be defined as the relative fluorescent signal produced when the specific antigen, e.g., an HbS hemoglobin variant, is bound versus another antigen, e.g., a wildtype hemoglobin. An antibody is considered to be specific for an antigen if it exhibits a 2-fold, typically at least a 3- or 4-fold increase, in reactivity for the reference antigen compared to another antigen that is tested.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of epitope mapping are well known in the art (see, e.g., Epitope Mapping Protocols in Methods in Molecular Biology, Vol. 66, Glenn E. Morris, Ed (1996)). A "minimal" epitope in the current invention is typically determined by measuring binding of the antibody to overlapping peptides covering the entire amino acid sequence of beta or alpha globin and identifying the amino acid sequence shared by all bound peptides. Important amino acids in the "minimal" epitope are typically identified by alanine scanning.

As understood in the art, a "minimal" epitope may include substitutions, e.g., at positions that are not important for binding, e.g., as determined using alanine scanning Such substitutions include conservative substitutions where the alteration results in the substitution of an amino acid with a chemically similar amino acid. Conservative substitution tables providing functionally similar amino acids are well known in the art. The following are examples from among the twenty common naturally occurring amino acids of amino acids that may be substituted for one another: alanine and glycine; aspartic acid and glutamic acid; asparagine and glutamine; arginine and lysine; serine and threonine. Other conservative substitutions include substitutions of one amino acid in the following group with another amino acid in the group: isoleucine, leucine, methionine, and valine. Phenylalanine, tyrosine, and tryptophan are also examples of residues that may be substituted for one another.

Table 1 provides examples of immunogens utilized to generate specific monoclonal antibodies to hemoglobin and hemoglobin variants.

TABLE 1

Examples of Peptide Immunogens

| Hemoglobin target | Peptide Name | sequence | SEQ ID NO: |
|---|---|---|---|
| Hemoglobin | H1 | H2N-VHLTPEEKSAVTALW-C-CONH2 | 23 |
| and | H2 | H2N-VHLTPEEASASTASW-C-CONH2 | 24 |
| variants | H2bis | H2N-VHLTPEEKSASTASW-C-CONH2 | 25 |
| HbS | H3 | H2N-VHLTPVEKSAVTALW-C-CONH2 | 26 |
| HbC | H4 | H2N-VHLTPKEKSAVTALW-C-CONH2 | 27 |
| HbE | H5 | H2N-CYG-NVDEVGGKALGRLLV-CONH2 | 28 |
| | H5bis | H2N-CYG-VTALWGKVNVDEVGGK-CONH2 | 29 |
| | H10 | H2N-C-Hx-EVGGKALG-CONH2 | 30 |
| | H10bis | H2N-EVGGKALG-Hx-C-CONH2 | 31 |
| HbD | H6 | H2N-CYG-VLAHHFGKQFTPPVQAA-CONH2 | 32 |
| | H6bis | H2N-QFTPPVQAAYQKVVAGV-GYC-CONH2 | 33 |
| | H9 | H2N-GKQFTGKQFTGKQFT-GYC-CONH2 | 34 |
| | H11 | H2N-C-Hx-HFGKQFTP-CONH2 | 35 |
| | H11bis | H2N-HFGKQFTP-Hx-C-CONH2 | 36 |
| $HbA1_c$ | GP1 | Glucose-HN-VHLTPEE-Hx-C-CONH2 | 37 |
| | GP3 | 1-deoxyfructopyranosyl-HN-VHLTPEE-Hx-C-CONH2 | 38 |
| | Glycated H2 | Glucose-HN-VHLTPEEASASTASW-C-CONH2 | 39 |

Table 2 provides examples of immunization regimens utilized to generate specific monoclonal antibodies to hemoglobin and hemoglobin variants.

TABLE 2

Examples of immunization regimens

| Injection sequence | HbS | HbC | HbE | HbD | HbAlc | HbA and variants |
|---|---|---|---|---|---|---|
| 1 | native HbS antigen | H4-KLH | H5bis-KLH | denatured HbD + H6-KLH | GP3-KLH | native HbA0 |
| 2 | H3-KLH | H4-KLH | H5bis-KLH | denatured HbD + H6-KLH | GP3-KLH | H1-KLH |
| 3 | H3-KLH | H4-KLH | H5bis-KLH | denatured HbD + H6-KLH | GP3-KLH | native HbA0 |
| 4 | denatured HbS + H3-KLH | denatured HbC | H5bis-KLH | denatured HbD + H6-KLH | GP3-KLH | H1-KLH |
| 5 | denatured HbS + H3-KLH | H4-KLH | denatured HbE | denatured HbD + H6-KLH | | |
| 6 | denatured HbS + H3-KLH | H4-KLH | denatured HbE | denatured HbD | | |
| 7 | | | denatured HbE | denatured HbD + H6-KLH | | |
| 8 | | | H5bis-KLH | denatured HbD + H6-KLH | | |
| 9 | | | H5bis-KLH | denatured HbD + H6-KLH | | |
| 10 | | | denatured HbE + H5bis-KLH | denatured HbD + H6-KLH | | |
| 11 | | | denatured HbE + H5bis-KLH | | | |
| 12 | | | denatured HbE + H5bis-KLH | | | |
| Route of injection | Subcutaneous And intraperitoneal | Subcutaneous and intraperitoneal | Subcutaneous and intraperitoneal | Subcutaneous and intraperitoneal | Intraperitoneal | Subcutaneous and intraperitoneal |

HbS Antibodies

Hemoglobin variant HbS has a point mutation in which glutamic acid at position 6 of the hemoglobin beta chain is mutated to a valine.

Anti-HbS antibodies of the invention that are selective for HbS have the following binding characteristics: the antibody bind to HbS with an affinity that is at least 100-fold lower (i.e., better) than its affinity for HbC and HbA0. In some embodiments, the antibody binds to the minimal HbS epitope $^{5}$PVEKSAVT$^{12}$ (SEQ ID NO:40). Such an antibody may have a reactivity in which the reactivity is such that the valine at position 6 can be replaced by an isoleucine, but replacement with other amino acids at that position results in a 2-fold, often a three-fold or greater decrease in reactivity. In some embodiments, $^{3}$LTP$^{5}$, $^{7}$E, and $^{10}$A are also important for binding.

In some embodiments, the antibody binds to a minimal epitope $^{3}$LTPVEKSAVT$^{12}$ (SEQ ID NO:3). In some embodiments, the antibody may have a reactivity where the valine at position 6 can be replaced by an isoleucine or alanine, but substitution with other amino acids at that positions results in a two-fold, often a three-fold or greater decrease in reactivity. In some embodiments, $^{2}$HLTPVEK$^{8}$ (SEQ ID NO:41) and $^{10}$A are also important for binding.

In some embodiments, an antibody that binds to an HbS minimal epitope, e.g., $^{5}$PVEKSAVT$^{12}$ (SEQ ID NO:40). may bind to variants of the HbS minimal epitope that have the valine at position 6, such as a minimal epitope comprising $^{5}$PVEX$_2$X$_3$A$^{10}$ (SEQ ID NO:4), where $X_2$ and $X_3$ can be independently selected from the 20 common naturally occurring amino acids, e.g., conservative substitutions of K and S, respectively.

The antibody typically is an IgG, e.g., the antibody may have an IgG1, IgG2, or IgG3 isotype. In some embodiments, the light chain constant region is a kappa chain. In other embodiments, the light chain constant region may be a lambda chain.

In one embodiment, an HbS antibody of the invention is raised against the immunogen HbS and H3-KLH: $H_2N$-VHLTPVEKSAVTALW-C—$CONH_2$ (SEQ ID NO:26). In other embodiments, the immunogen is either a combination of H3-KLH: $H_2N$-VHLTPVEKSAVTALW-C—$CONH_2$ (SEQ ID NO:26) and purified native and/or denatured HbS protein, or sequential or serial immunizations using the individual components of the above immunogens. Carrier proteins other than KLH can also be used. Examples are albumin and ovalbumin, and further examples will be readily apparent to those skilled in the art.

As understood in the art and illustrated by Table 1 above, many variations of immunogens can be used to obtain the desired antibody. For example, peptide immunogen H3-KLH: $H_2N$-VHLTPVEKSAVTALW-C—$CONH_2$ (SEQ ID NO:26) may also have a C-terminal carboxylate, rather than a C-terminal carboxamide. In some embodiments, the cysteine linker moiety may be spaced with a Hx residue, which is 6-amino hexanoic acid, or a spacer, such as a Gly-Gly spacer sequence may be employed. Further, the peptide sequence may also vary.

An anti-HbS antibody typically binds to both glycated and nonglycated forms of HbS with similar affinity. For example, an anti-HbS antibody typically selectively binds to both glycated and non-glycated HbS with a binding reactivity in which there is less than a three-fold reactivity difference, typically less than a two-fold reactivity difference, between binding to glycated vs. non-glycated HbS.

Anti-HbC Antibodies

Hemoglobin variant HbC has a lysine substituted for the glutamic acid at position 6 of the hemoglobin beta chain. An anti-HbC monoclonal antibody for use in the invention typically binds to HbC with an affinity that is at least 100 times greater that the affinity of the antibody for HbS and HbA0. In some embodiments, the monoclonal antibody binds to the minimal epitope $^{4}$TPKEKSAVT$^{12}$ (SEQ ID NO:1). In some embodiments, the antibody has a binding specificity such that residues important for binding are residues $^{3}$LT$^{4}$ and $^{6}$K. In some embodiments, residues important for binding may be $^{3}$LT$^{4}$ and $^{6}$KE$^{7}$. The binding specificity also allows for substitution of lysine by arginine or histidine at position 6, but substitution of other amino acids results in at least a 2-fold, typically a 3-fold or greater loss in reactivity. In other embodiments, the reactivity of the HbC antibody is such that the lysine at position 6 may be substituted with an arginine, tyrosine, asparagine, glutamine or glycine, but substitution with other amino acids residues results in a loss of reactivity.

In some embodiments, an antibody that binds to a HbC minimal epitope, e.g., $^{4}$TPKEKSAVT$^{12}$ (SEQ ID NO:1), may bind to variants of the HbC minimal epitope that have the K at position 6, such as a minimal epitope comprising $^{4}$TX$_1$KE$^{7}$ or $^{3}$LTX$_1$KE$^{7}$ (SEQ ID NO:2) where $X_1$ can be one of the 20 common naturally occurring amino acids.

The antibody typically is an IgG, e.g., the antibody may have an IgG1, IgG2, or IgG3 isotype. In some embodiments, the light chain constant region is a kappa chain. In other embodiments, the light chain constant region may be a lambda chain.

An antibody of the invention may be raised against the immunogen H4-KLH: $H_2N$-VHLTPKEKSAVTALW-C—CONH$_2$ (SEQ ID NO:27). Examples of other peptide immunogens are listed in Table 1, and here again, other common carrier proteins can be used in place of KLH. In some embodiments, the immunization is performed using a combination of the peptide and purified native and/or denatured HbC protein. In some embodiments, sequential or serial immunizations are performed using the individual components of the above immunogens. An exemplary immunization protocol is shown in Table 2. As explained above in the section relating to anti-HbS antibodies, one of skill can readily design other immunogenic peptides to obtain an antibody having the desired HbC binding specificity.

An anti-HbC antibody typically binds to both glycated and nonglycated forms of HbC with similar affinity. For example, an anti-HbC antibody typically selectively binds to both glycated and non-glycated HbC with a binding reactivity in which there is less than a three-fold reactivity difference, typically less than a two-fold reactivity difference, between binding to glycated vs. non-glycated HbC.

Anti-HbE Antibodies

HbE has a lysine substituted for the glutamic acid at position 26 of the hemoglobin beta chain. An anti-HbE monoclonal antibody of the invention is typically at least 4-fold or 5-fold more reactive, often at least 10-fold more reactive, with HbE in comparison to HbA. In some embodiments, the monoclonal antibody binds to the minimal epitope $^{22}$EVGGK$^{26}$ (SEQ ID NO:6). In some embodiments such an anti-Hb-E antibody has a binding specificity for $^{22}$EVGGK$^{26}$ (SEQ ID NO:6) that is dependent on $^{22}$E and in which $^{21}$D, $^{23}$V, and $^{26}$K are important for binding. In some embodiments, the antibody has a binding specificity that is dependent on E22 and in which D21, V23 and K26 are important for binding. In some embodiments, the antibody has a binding specificity such that substitution of the K at position 26 with S, T A, R, Q or G preserves at least 50%, typically at least 70% or greater of the binding activity. In some embodiments, substitution of the K at position 26 with S, T, A, R or V preserves at least 50%, typically at least 70% or greater, of the binding activity.

In some embodiments, an antibody that binds to a HbE minimal epitope, e.g., $^{22}$EVGGK$^{26}$ (SEQ ID NO:6) may bind to variants of the HbE minimal epitope that have the K at position 26, such as a minimal epitope comprising $^{21}$DEVGGK$^{26}$ (SEQ ID NO:7) or $^{22}$EVX$_4$X$_5$K$^{26}$, where $X_4$ and $X_5$ can be independently selected from the 20 common naturally occurring amino acids, e.g., conservative substitutions of G.

The antibody typically is an IgG, e.g., the antibody may have an IgG1, IgG2, or IgG3 isotype. In some embodiments, the light chain constant region is a kappa chain. In other embodiments, the light chain constant region may be a lambda chain.

An anti-HbE antibody of the invention can be obtained, e.g., using the immunogen H5bis-KLH: $H_2N$-CYG-VTALWGKVNVDEVGGK-CONH$_2$ (SEQ ID NO:29). In some embodiments, the antibody is raised against an immunogen H5bis-KLH: $H_2N$-CYG-VTALWGKVNVDEVGGK-CONH$_2$ (SEQ ID NO:29) with mixtures or sequential injections of peptide, native HbE antigen, and HbE denatured antigen. Examples of peptide immunogens are provided in Table 1. Peptide immunogens can be used in combination with one another, either with or without denatured or native HbE. Exemplary immunization protocols are provided in Table 2. As explained above in the section relating to anti-HbS antibodies, one of skill can readily design other immunogenic peptides to obtain an antibody having the desired HbE binding specificity. The reader is again referred to Table 1 for examples of other peptide immunogens.

An anti-HbE antibody typically binds to both glycated and nonglycated forms of HbE with similar affinity. For example, an anti-HbE antibody typically selectively binds to both glycated and non-glycated HbE with a binding reactivity in which there is less than a three-fold reactivity difference, typically less than a two-fold reactivity difference, between binding to glycated vs. non-glycated HbE.

Anti-HbD Antibodies

HbD has a glutamine substituted for a glutamic acid at position 121 of the hemoglobin beta chain. An anti-HbD monoclonal antibody of the invention is typically at least 3-fold, or greater more reactive with HbD in comparison to HbA. In some embodiments, the antibody binds to the minimal epitope $^{121}$QFTPP$^{125}$ (SEQ ID NO:8). In some embodiments, the antibody has a binding specificity where residues $^{119}$G, $^{121}$QF$^{122}$, and $^{124}$PP$^{125}$ are important for binding.

In some embodiments, an antibody that binds to a HbD minimal epitope, e.g., $^{121}$QFTPP$^{125}$ (SEQ ID NO:8), may bind to variants of the HbE minimal epitope that have the Q at position 121, such as a minimal epitope comprising $^{119}$GX$_6$QFX$_7$PP$^{125}$ (SEQ ID NO:9) or $^{121}$QFX$_7$PP$^{125}$ (SEQ ID NO:10), where $X_6$ and $X_7$ can be independently selected from the 20 common naturally occurring amino acids, e.g., conservative substitutions of K and T, respectively.

The antibody typically is an IgG, e.g., the antibody may have an IgG1 or IgG2 isotype. In some embodiments, the light chain constant region is a kappa chain. In other embodiments, the light chain constant region may be a lambda chain.

An anti-HbD antibody of the invention can be raised, for example, against the immunogen H6-KLH: $H_2N$-CYGVLAHHFGKQFTPPVQAA-$CONH_2$ (SEQ ID NO:32), or against mixtures of native and/or denatured HbD and H6-KLH: $H_2N$-CYGVLAHHFGKQFTPPVQAA-$CONH_2$ (SEQ ID NO:32), or by using combinations of, or sequential injections of, the various immunogens. Other immunogenic peptides useful in obtaining an antibody having the desired HbD binding specificity will be readily apparent to those skilled in the art.

An anti-HbD antibody typically binds to both glycated and nonglycated forms of HbD with similar affinity. For example, an anti-HbD antibody typically selectively binds to both glycated and non-glycated HbD with a binding reactivity in which there is less than a three-fold reactivity difference, typically less than a two-fold reactivity difference, between binding to glycated vs. non-glycated HbD.

Pan-Reactive Antibodies

The invention also provides pan-reactive antibodies for use in the invention. Such antibodies bind to multiple forms of hemoglobin. Pan-reactive antibodies can be produced using a number of different immunogens, including H5bis-KLH: $H_2N$-CYGVTALWGKVNVDEVGGK-$CONH_2$ (SEQ ID NO:29) or H1-KLH: $H_2N$-VHLTPEEK-SAVTALW-C—$CONH_2$ (SEQ ID NO:23). Such peptide immunogens can be injected either in a mixture with native or denatured $HbA_0$, or sequentially with native and/or denatured HbA0. As understood in the art, any number of Hb immunogens can be used to obtain a Hb antibody that selectively binds to $HbA_0$ as well as Hb variants. Pan-reactive antibodies may be monoclonal or polyclonal. Pan-reactive antibodies can also be obtained by immunization with native or denatured hemoglobin without using peptide immunogens.

In some embodiments, a pan-reactive polyclonal antibody for use in the invention binds to one ore more epitopes present in the following regions of alpha globin and beta globin: alpha globin $^{49}$SHGSAQVKGHGKKVADALTNAVAHVDDMPNALSALSDHLHAHKLRRVDPV$^{96}$ (SEQ ID NO:11), beta globin $^{15}$WGKVNVDEVGGEALG$^{29}$ (SEQ ID NO:12), $^{45}$FGDLSTP$^{51}$ (SEQ ID NO:13), and $^{76}$AHLDNLKGTFAT$^{87}$ (SEQ ID NO:14).

In one embodiment, a pan-reactive antibody binds to the beta globin epitope $^{9}$SAVTALWGKVNV$^{20}$ (SEQ ID NO:15). In some embodiments, the antibody binds to the beta globin epitope $^{11}$VTALW$^{15}$ (SEQ ID NO:17). In some embodiments $^{11}$VT$^{12}$ and $^{14}$Lw$^{15}$ are important for binding.

In some embodiments, a pan-reactive antibody binds to beta and alpha globin epitopes that contain the following sequences: a beta globin minimal epitope $^{8}$KSAVTALWGKVNV$^{20}$ (SEQ ID NO:16), a beta globin minimal epitope $^{58}$PKVKAHGKKVLGAF$^{71}$ (SEQ ID NO:20) and a beta globin minimal epitope $^{87}$TLSELHCDKLHVDPENFR$^{104}$ (SEQ ID NO:21). In some embodiments residues $^{13}$ALWG$^{16}$ (SEQ ID NO:18) are important for binding.

The antibody typically is an IgG, e.g., the antibody may have an IgG1, IgG2, or IgG3 isotype. In some embodiments, the light chain constant region is a kappa chain. In other embodiments, the light chain constant region may be a lambda chain.

A pan-reactive antibody used in the invention is broadly reactive to hemoglobin and binds to both glycated and non-glycated forms of hemoglobin A and variants such as HbS, HbC, HbD, and HbE.

In some embodiments of the invention, a pan-reactive antibody that binds to multiple forms of hemoglobin is used as a labeled binding member that binds to all of the analytes, thereby labeling the bound analytes. Thus, for example, a labeled pan-reactive polyclonal antibody that binds to the epitopes: alpha globin $^{49}$SHGSAQVKGHGKKVADALTNAVAHVDDMPNALSALSDHLHAHKLRRVDPV$^{96}$ SEQ ID NO:11), beta globin $^{16}$GKVNVDEVGGEALG$^{29}$ SEQ ID NO:42), $^{46}$GDLSTP$^{51}$ SEQ ID NO:43), and $^{78}$LDNLKGTFAT$^{87}$ (SEQ ID NO:44) can be used as a universal detection antibody that binds to all of the analytes (forms of hemoglobin) being assayed, thereby labeling the bound analytes Anti-$HbA_{1c}$ Antibodies The invention additionally provides anti-$HbA_{1c}$ antibodies that have a binding specificity for glycated hemoglobin. Such antibodies can be produced using an immunogen such as GP3-KLH: 1-deoxyfructopyranosyl-HN-VHLTPEE-Hx-C—$CONH_2$ (SEQ ID NO:38). The antibody can be an IgG, for example, and can have an $IgG_1$, $IgG_2$, or $IgG_3$ isotype. In some embodiments, the light chain constant region is a lambda chain. In other embodiments, the light chain constant region is a kappa chain.

An anti-$HbA_{1c}$ antibody of the invention is highly specific for glycated hemoglobin, including $HbA_{1c}$, $HbS_{1c}$, $HbD_{1c}$, $HbE_{1c}$, and $HbC_{1c}$, and does not recognize non-glycated forms of hemoglobin (i.e., the antibody has at least a 100-fold greater affinity for $HbA_{1c}$, $HbS_{1c}$, $HbD_{1c}$, $HbE_{1c}$, and $HbC_{1c}$ than for the non-glycated forms). Such antibodies typically have a binding specificity for glycated N-terminal peptide where both glycated valine 1 and histidine 2 are important residues for binding.

An $A_{1c}$ monoclonal antibody has a binding specificity in competitive binding experiments such that the glycated peptide GP3 (1-deoxyfructopyranosyl-HN-VHLTPEE-Hx-C—$CONH_2$; SEQ ID NO:38) competes for binding to native $HbA_{1c}$, but unglycated peptides such as RW1a (VHLTPEE-$CONH_2$; SEQ ID NO:45) do not.

HbF and $HbA_2$ Antibodies

HbF and $HbA_2$ can also be assayed using the methods of the invention. Antibodies that selectively bind to HbF relative to $HbA_0$ or other Hb proteins; or to $HbA_2$ relative to $HbA_0$ or other Hb proteins, can be obtained using immunogens comprising peptide sequences that are specific to HbF or sequences that are specific to $HbA_2$, as there are multiple differences in the delta and gamma chains relative to the $A_0$ beta chain.

Generation of Antibodies

The anti-hemoglobin antibodies of the invention can be raised against hemoglobin proteins, or fragments, or produced recombinantly. Any number of techniques well known in the art can be used to determine antibody binding specificity. See, e.g., Harlow & Lane, Antibodies, A Laboratory Manual (1988) for a description of immunoassay formats and conditions that can be used to determine specific immunoreactivity of an antibody In some embodiments, an antibody for use in the invention, e.g., a hemoglobin antibody that binds various forms of hemoglobin, a hemoglobin antibody specific for a variant, or a hemoglobin antibody specific for glycated hemoglobin, is a polyclonal antibody. For example, an antibody specific for a hemoglobin variant can be an affinity-purified monospecific polyclonal antibody. Methods of preparing polyclonal antibodies are known to the skilled artisan (e.g., Harlow &

Lane, Antibodies, A Laboratory manual (1988); Methods in Immunology). Polyclonal antibodies can be raised in a mammal by one or more injections of an immunizing agent and, if desired, an adjuvant.

In some embodiments, the antibody for use in the invention, e.g., an antibody that binds to multiple forms of hemoglobin, an antibody that is specific for a hemoglobin variant (and the glycated hemoglobin variant), or an antibody that is specific for glycated hemoglobin, is a monoclonal antibody. Monoclonal antibodies may be prepared using hybridoma methods, such as those described by Kohler & Milstein, *Nature* 256:495 (1975). In a hybridoma method, a mouse, rat, rabbit, or other appropriate host animal, is typically immunized with an immunizing agent to elicit lymphocytes that produce or are capable of producing antibodies that will specifically bind to the immunizing agent. Alternatively, the lymphocytes may be immunized in vitro.

As stated above, antibodies of the invention can be generated using any number of immunogens and immunization protocols. In some embodiments, the immunogen is a peptide that is administered in combination with a native or denatured hemoglobin protein. As understood in the art, an immunogen may be administered multiple times. In embodiments in which a combination is employed, the combination of antigens may be administered concurrently, or sequentially, in any order. In some embodiments, a peptide immunogen is a KLH conjugate, however, carrier proteins other than KLH can be used, e.g., BSA conjugates can be used.

Assay Conditions Using the Antibodies

In the practice of this invention, hemoglobin $A_{1c}$, hemoglobin variants, and total hemoglobin can be measured via a variety of immunoassay formats. One example is the sandwich format, in which a specific antibody to the analyte is attached to the solid phase bead, and detection is accomplished by interrogating the beads with one or more antibodies to the hemoglobin species. A universal antibody which binds to all hemoglobin species can be used for the interrogation, but two or more detection antibodies can also be used. An example is shown in FIG. 1, where individual antibodies are used that are specific to total hemoglobin, $HbA_{1c}$, and the four most prevalent hemoglobin variation species HbS, HbC, HbE, and HbD, respectively, are bound to separate subpopulations of beads, while a universal antibody that binds to all hemoglobin species and that bears phycoerythrin (PE) as a label is used. In a sandwich assay format, the quantity of antibody for each assay is selected such that the analyte (the particular form of hemoglobin to which the assay is directed) is in excess, so that the antibodies are the limiting reagents in the binding reactions. Competition between the antibody for total hemoglobin and the antibodies for the individual hemoglobins, for example, is thereby minimized. By adjusting the assay parameters and selection of the appropriate antibodies in a manner within the skill of the art, however, a competitive assay format can also be utilized for multiplexed detection of hemoglobin species.

While the multiplex assay can be utilized on mammalian blood samples in general, the assay is of particular value to samples of human blood. Blood samples are prepared for the assay by lysis of the cells and dilution of the lysate to a concentration suitable for immunoassay. Each of these steps is performed by methods known in the art. Dilution can be achieved with water, solutions containing saponin, or any other diluent that will not affect the hemoglobins or their immunological binding activity, and the degree of dilution can vary widely. In most cases, the dilution will be within the range of about 1:25 to about 1:3000. The hemoglobins in the lysate can be denatured before or after dilution of the lysate and used in the assay, or the lysate can be used without denaturation of the hemoglobins. In most cases, denaturation is preferred, and can be performed by methods known in the art.

The levels of $HbA_{1c}$ and each of the variants are preferably each expressed as a percentage of total hemoglobin in the sample. For determinations of degrees of glycation in the presence of a hemoglobin variant, the invention offers three options. One option, which is compatible with the currently accepted method, is the determination of the $HbA_{1c}$ level by the result from the $HbA_{1c}$ bead only, normalized to total hemoglobin. The second option is the determination of the total hemoglobin glycation by adding the percent of the glycated form of the variant to the percent $HbA_{1c}$. The third option, which is useful in the event that the determination of $HbA_{1c}$ is adversely affected by the presence of the variant, is to adjust the as-measured percent $HbA_{1c}$ by a correction factor that is a function of the detected level of the variant. The function can be determined empirically by a relation that can be independently determined by separate assays, including non-multiplex assays. The correction factor can be one that is applied either to the $HbA_{1c}$ concentration after the concentration has been normalized with respect to total hemoglobin, or to the concentration prior to normalization.

To illustrate the correction of the $HbA_{1c}$ value, assays were performed on samples from ten patients, using both a bead-based assay (BioPlex 2200 of Bio-Rad Laboratories, Inc., Hercules, Calif., USA) in accordance with the present invention and an HPLC assay (Variant™ II of Bio-Rad Laboratories, Inc.), both assays determining percent $HbA_{1c}$ as a function of increasing percentage of HbC. The results are shown in Table 3 and in FIG. 2, in which the "Difference Ratio"=(% $A_{1c}$ Variant II—% $A_{1c}$ BioPlex 2200)/(% $A_{1c}$ Variant II).

TABLE 3

| | | % $A_{1c}$ | | | | Difference from Target | |
|---|---|---|---|---|---|---|---|
| Patient ID | % HbC | BioPlex 2200 | Variant II (Target) | Difference Ratio | Adjusted BioPlex Value | Adjusted | Unadjusted |
| PT 200 | 31.8 | 6.06 | 5.9 | −0.03 | 5.73 | 0.17 | −0.16 |
| PT 219 | 32.1 | 6.30 | 5.8 | −0.09 | 5.98 | −0.18 | −0.50 |
| PT 265 | 33.7 | 5.71 | 5.4 | −0.06 | 5.37 | 0.03 | −0.31 |
| PT 622 | 34.1 | 6.20 | 5.9 | −0.05 | 5.87 | 0.03 | −0.30 |
| PT 658 | 33.9 | 5.92 | 5.9 | 0.00 | 5.59 | 0.31 | −0.02 |
| PT 667 | 33.5 | 6.00 | 5.8 | −0.03 | 5.67 | 0.13 | −0.20 |
| PT m832 | 32.1 | 6.14 | 6.1 | −0.01 | 5.81 | 0.29 | −0.04 |

TABLE 3-continued

| | % $A_{1c}$ | | | | | | |
|---|---|---|---|---|---|---|---|
| Patient ID | % HbC | BioPlex 2200 | Variant II (Target) | Difference Ratio | Adjusted BioPlex Value | Difference from Target Adjusted | Difference from Target Unadjusted |
| PT m837 | 37.6 | 5.80 | 5.5 | −0.05 | 5.47 | 0.03 | −0.30 |
| PT m908 | 39.2 | 5.37 | 4.6 | −0.17 | 5.03 | −0.43 | −0.77 |
| PT m923 | 41.1 | 5.53 | 4.8 | −0.15 | 5.19 | −0.39 | −0.73 |
| | | | | average difference → | | 0.00 | −0.33 |

While various mathematical models can be used to quantify the relationship of the percent $HbA_{1c}$ difference as a function of percent hemoglobin C (or any hemoglobin variant), the mathematical model used in this example is a simple linear regression model. Using this model, the values obtained from the BioPlex 2200 immunoassay can be corrected to yield a result comparable to the reference method. This is demonstrated by the average difference of the adjusted BioPlex 2200 percent $HbA_{1c}$ value relative to the target percent $HbA_{1c}$ value determined by the reference Variant II method. In Table 3 and FIG. 2, the average difference is zero for the adjusted $HbA_{1c}$ values compared to −0.33 for the corresponding unadjusted values. The corrected $HbA_{1c}$ value shown in the table provides a better estimate of the glycemic index of the individual.

Figure 2:
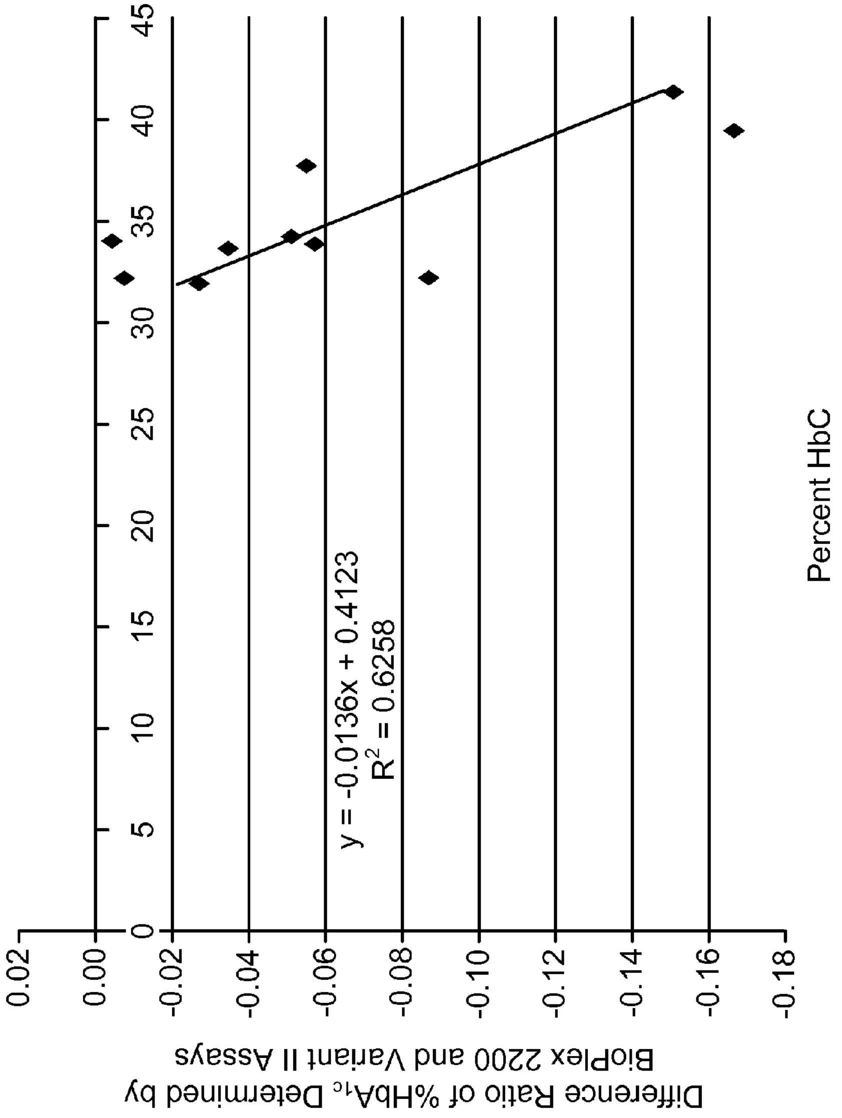
FIG. 2 is a plot of comparative data between a series of multiplex assays in accordance with the present invention and a series of HPLC assays.

The BioPlex 2200 bead-based immunoassay used in the obtaining the data in Table 3 and FIG. 2 utilizes an antibody that binds $HbA_{1c}$ and all hemoglobin variants including HbS, HbC, HbD, and HbE. All glycated variants and $HbA_0$ are bound with approximately the same affinity and avidity by the antibody. The immunoassay result thus represents total glycated hemoglobin, which in the case of a heterozygous hemoglobin AS variant, is the combined value that includes both the $HbA_{1c}$ and $HbS_{1c}$ species. In individuals exhibiting a hemoglobin variant phenotype, the proportion of the glycated hemoglobin corresponding to the variant provides an improved measure of glycemic status. The percent $HbS_{1c}$ in the sample is obtained by multiplying the total percent $HbA_{1c}$ plus $HbS_{1c}$ value by the proportion of HbS in the sample. For example, for a patient sample with a total glycated hemoglobin value of 5.54% (consisting of $HbA_{1c}$ and $HbS_{1c}$), multiplying this value by the proportion of HbS in the sample of 38.8% yields a value for $HbS_{1c}$ of 2.14%. The remainder of the glycated material is $HbA_{1c}$ at 3.4%. This again is but one mathematical model; more sophisticated mathematical models can be used to provide more accurate results as needed.

The beads that provide the surfaces on which the binding reactions occur in the practice of this invention can be formed of any material that is inert to the assay materials and to the components of the sample itself, and that is solid and insoluble in the sample and in any other solvents or carriers used in the assay. Polymers are preferred, and the beads are preferably microparticles. The polymeric can be any material that can be formed into a microparticle and is capable of coupling to an antibody at a region on the antibody that does not interfere with the antigen-binding regions of the antibody. In embodiments in which fluorescent labels are used, preferred polymers are also those that produce at most a minimal level of autofluorescence. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. Magnetic beads can also be used.

Attachment of the antibodies to the surfaces of the beads can be achieved by electrostatic attraction, specific affinity interaction, hydrophobic interaction, or covalent bonding. Covalent bonding is preferred. Functional groups for covalent bonding can be incorporated into the polymer structure by conventional means, such as the use of monomers that contain the functional groups, either as the sole monomer or as a co-monomer. Examples of suitable functional groups are amine groups ($—NH_2$), ammonium groups ($—NH_3^+$ or $—NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid. Linking groups can also be used for increasing the density of the antibodies on the solid phase surface and for decreasing steric hindrance to increase the range and sensitivity of the assay. Examples of suitable useful linking groups are polylysine, polyaspartic acid, polyglutamic acid and polyarginine.

The size range of the beads can vary and particular size ranges are not critical to the invention. In most cases, the aggregated size range of the beads lies within the range of from about 0.3 micrometers to about 100 micrometers in diameter, and preferably within the range of from about 0.5 micrometers to about 40 micrometers.

Multiplexing with the use of beads in accordance with this invention is achieved by assigning the beads to two or more groups, also referred to herein as bead sets or subpopulations. Each group will have affixed thereto an antibody selected for either a hemoglobin variant, a glycated variant, $HbA_{1c}$, or total hemoglobin, and will be separable or at least distinguishable from the other group(s) by a "differentiation parameter." The "differentiation parameter" can be any distinguishable characteristic that permits separate detection of the assay result in one group from those in the other groups. One example of a differentiation parameter is the particle size, with each group having a size range that does not overlap with the size ranges of the other groups. The widths of the size ranges and the spacing between mean diameters of different size ranges are selected to permit differentiation of the groups by flow cytometry according to size, and will be readily apparent to those skilled in the use of and instrumentation for flow cytometry. In this specification, the term "mean diameter" refers to a number average diameter. In most cases, a preferred size range width is one with a CV of about ±5% or less of the mean diameter, where CV is the coefficient of variation and is defined as the standard deviation of the particle diameter divided by the mean particle diameter times 100 percent. The minimum spacing between mean diameters among the various size ranges can vary depending on the size distribution, the ease of segregating beads by size for purposes of attaching different antibodies, and the type and sensitivity of the flow cytometry equipment. In most cases, best results will be achieved when the mean diameters of different size ranges are spaced apart by at least about 6% of the mean diameter of one of the size ranges, preferably at least about 8% of the mean diameter of one of the size ranges and most preferably at least about 10% of the mean diameter of one of the size ranges. Another preferred size range width relation is that in which the standard deviation of the particle diameters within each size range is less than one third of the separation of the mean diameters of adjacent size ranges.

Another example of a differentiation parameter that can be used to distinguish among the various groups of beads is fluorescence. Differentiation by fluorescence is accomplished by incorporating fluorescent materials in the beads, the materials having different fluorescent emission spectra for each group of beads and being distinguishable on this basis.

Fluorescence can thus be used both as a differentiation parameter and as a means for detecting that binding has occurred in the assays performed on the beads. The latter can be achieved by fluorescent labels serving as assay reporters. Thus, while individual groups can be distinguished by emitting different emission spectra, and the emission spectra used for group differentiation purposes can themselves differ from the emission spectra of the assay reporters. An example of a fluorescent substance that can be used as a differentiation parameter is fluorescein and an example of a substance that can be used for the assay detection is phycoerythrin. Different bead groups can be distinguished from each other by being dyed with different concentrations of fluorescein. Different bead groups can be distinguished by using fluorescent materials that have different fluorescence intensities or that emit fluorescence at different wavelengths. The dyes can also be used in combinations to produce a plurality of fluorescent emissions at different wavelengths, and the wavelength difference can be used both as the differentiation parameter and as a means of distinguishing the differentiation parameter from the assay reporter.

Still other examples of useful differentiation parameters are light scatter, light emission, or combinations of light scatter and emission. Side-angle light scatter varies with particle size, granularity, absorbance and surface roughness, while forward-angle light scatter is mainly affected by size and refractive index. Any of these qualities can thus be used as the differentiation parameter.

According to one means of differentiation, the beads will have two or more fluorochromes incorporated within them so that each bead in the array will have at least three distinguishable parameters associated with it, i.e., side scatter together with fluorescent emissions at two separate wavelengths. A red fluorochrome such as Cy5 can thus be used together with an orange fluorochrome such as Cy5.5. Additional fluorochromes can be used to expand the system further. Each bead can thus contain a plurality of fluorescent dyes at varying wavelengths.

Still another example of a differentiation parameter that can be used to distinguish among the various groups of beads is absorbance. When light is applied to beads the absorbance of the light by the beads is indicated mostly by the strength of the laterally (side-angle) scattered light while the strength of the forward-scattered light is relatively unaffected. Consequently, the difference in absorbance between various colored dyes associated with the beads is determined by observing differences in the strength of the laterally scattered light.

A still further example of a differentiation parameter that can be used to distinguish among the various groups of beads is the number of beads in each group. The number of beads of each group in an assay is varied in a known way, and the count of beads having various assay responses is determined. The various responses are associated with a particular assay by the number of beads having each response.

As the above examples illustrate, a wide array of parameters or characteristics can be used as differentiation parameters to distinguish the beads of one group from those of another. The differentiation parameters may arise from size, composition, physical characteristics that affect light scattering, excitable fluorescent or colored dyes that impart different emission spectra and/or scattering characteristics to the beads, or different concentrations of one or more fluorescent dyes. When the differentiation parameter is a fluorescent dye or color, it can be coated on the surface of the beads, embedded in the beads, or bound to the molecules of the bead material. Thus, fluorescent beads can be manufactured by combining the polymer material with the fluorescent dye, or by impregnating the beads with the dye. Beads with dyes already incorporated and thereby suitable for use in the present invention are commercially available, from suppliers such as Spherotech, Inc. (Libertyville, Ill., USA) and Molecular Probes, Inc. (Eugene, Oreg., USA). A list of vendors of flow cytometric products can be found on the Internet, e.g., at the world wide web molbio.princeton.edu/facs/FCMsites.html site.

Detection and differentiation in accordance with this invention are performed by flow cytometry. Methods of and instrumentation for flow cytometry are known in the art, and those that are known can be used in the practice of the present invention. Flow cytometry in general resides in the passage of a suspension of beads or microparticles as a stream past a light beam and electro-optical sensors, in such a manner that only one particle at a time passes through the region. As each particle passes this region, the light beam is perturbed by the presence of the particle, and the resulting scattered and fluorescent light are detected. The optical signals are used by the instrumentation to identify the subgroup to which each particle belongs, along with the presence and amount of label, so that individual assay results are achieved. Descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory,* 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561,042 (published Feb. 13, 1980); and Steinkamp et al., *Review of Scientific Instruments* 44(9): 1301-1310 (1973).

Example 1

This example presents the binding activities of six hemoglobin candidate antibodies for use in the practice of this invention. The six antibodies are:

| | |
|---|---|
| 19E10-E7 (HbS specific) | 7B3-2C3-1G10 (HbD specific) |
| 12C8-A11 (HbC specific) | 13G7-E8-3H3 ($HbA_{1c}$ specific) |
| 4A10-2D6-2G8 (HbE specific) | 3E5-DLE10-3A3 (pan-reactive). |

19E10-E7 binds to a beta globin minimal epitope $^5$PVEKSAVT$^{12}$ (SEQ ID NO:40). $^5$PVE$^7$ and $A^{10}$ are important for binding. $L^3$ and $T^4$ also contribute to binding activity. Additional epitope mapping experiments showed that $V^6$ can be replaced with I without loss of binding activity.

12C8-A11 binds to a beta globin minimal epitope $^4$TPKEKSAVT$^{12}$ (SEQ ID NO:1). $T^4$ and $K^6$ are important for binding. $L^3$ also contributes to binding. Additional epitope mapping experiments showed that $K^6$ can be replaced with R without reducing binding activity.

4A10-2D6-2G8 binds a beta globin minimal epitope $^{22}$EVGGK$^{26}$ (SEQ ID NO:6). $^{22}$EV$^{23}$ and $K^{26}$ are important for binding. $D^{21}$ also contributes to binding. Additional epitope mapping experiments showed that $K^{26}$ can be replaced with S or T without loss of binding activity.

7B3-2C3-1G10 binds to a beta globin minimal eptiope $^{121}$QFTPP$^{125}$ (SEQ ID NO:8). $G^{119}$ also contributes to binding.

The antibody binding kinetics were analyzed using the ProteOn XPR36 (Bio-Rad Laboratories, Inc.) for protein-protein interactions. The different antibodies (10 μg of each) were amine-coupled to the sensor chip such that one antibody was immobilized per channel. Antigen was employed in the range of from 200 to 13 nM. The results of the kinetic analysis are summarized in Table 4 below.

Each antibody had a high affinity for its specific hemoglobin. The pan-reactive antibody also had good affinity constants to the different antigens, but lower than the affinity constant exhibited by the specific variant antibodies for their respective antigens. Except for 19E10-E7, all of the variant antibodies did not bind HbA0, so the affinity constants were essentially zero. For the 19E10-E7 anti-HbS antibody, a low level of binding to HbA0 was observed, with an affinity constant of 6.5 $10^{-7}$ M, which is 2 logs less than the affinity constant for HbS.

TABLE 4

Kinetics analysis for 6 specific monoclonal antibodies to hemoglobin and hemoglobin variants

| | $k_a$ (1/Ms) | $K_d$ (1/s) | $K_D$ (M) |
|---|---|---|---|
| 19E10-E7 | | | |
| HbS | 7.6 $10^4$ | 6.3 $10^{-4}$ | 8.3 $10^{-9}$ |
| 12C8-A11 | | | |
| HbC | 7.3 $10^4$ | 4.5 $10^{-4}$ | 6.1 $10^{-9}$ |
| 4A10-2D6 | | | |
| HbE | 7.1 $10^4$ | 6.2 $10^{-5}$ | 8.7 $10^{-10}$ |
| 7B3-2C3 | | | |
| HbD | 1.4 $10^5$ | 1.1 $10^{-3}$ | 7.4 $10^{-9}$ |
| 13G7-E8 | | | |
| $HbA_{1c}$ | 1.2 $10^4$ | 2.3 $10^{-5}$ | 1.9 $10^{-9}$ |

TABLE 4-continued

Kinetics analysis for 6 specific monoclonal antibodies to hemoglobin and hemoglobin variants

| | $k_a$ (1/Ms) | $K_d$ (1/s) | $K_D$ (M) |
|---|---|---|---|
| 3E5-DLE10 | | | |
| HbS | 3.9 $10^4$ | 7.9 $10^{-4}$ | 2.0 $10^{-8}$ |
| HbE | 2.9 $10^4$ | 4.4 $10^{-4}$ | 1.5 $10^{-8}$ |
| HbD | 3.4 $10^4$ | 1.0 $10^{-3}$ | 3.0 $10^{-8}$ |
| $HbA_{1c}$ | 3.7 $10^4$ | 9.4 $10^{-4}$ | 2.5 $10^{-8}$ |
| HbC | 4.5 $10^4$ | 7.4 $10^{-4}$ | 1.6 $10^{-8}$ |
| HbA0 | 1.4 $10^4$ | 3.4 $10^{-3}$ | 2.4 $10^{-7}$ |

Example 2

This examples demonstrates the measurement of hemoglobin $A_{1c}$ and hemoglobin variant proteins as percentages of total hemoglobin using a sandwich immunoassay in accordance with this invention. Solid phase capture bead immunoreagents were developed utilizing the six monoclonal antibodies specific to $HbA_0$, $HbA_{1c}$, HbS, HbC, HbE, and HbD described in Example 1.

Antibodies to each of the six target antigens were coupled covalently to paramagnetic beads. Each bead was dyed to contain a specific fluorescent signal that was unique to each antibody, to enable subsequent differentiation in a flow cytometry detector. The six antibody-coupled beads were mixed to create a multiplex bead reagent. A detection antibody reagent was prepared using a phycoerythrin-labelled polyclonal antibody with reactivity to all hemoglobin species. A diagram of the various beads and the species bound to each in the assay is shown in FIG. 1.

The assay was performed by adding samples of whole blood and calibrators (5 μL) to a solution of buffered denaturant (10 μL), to expose all of the epitopes of the hemoglobin species present in the samples in order to make them available for binding by the solid phase antibodies. After denaturation for 10 minutes at 37 degrees, the bead reagent (250 μL) was added to the samples, followed by an additional incubation for 20 minutes at 37 degrees. The reaction mixture was washed four times with phosphate-buffered saline containing 0.1% Tween-20 (PBST, 100 μL each) detergent to remove all of the unbound proteins from the sample, leaving the beads with their bound hemoglobin targets. The beads were re-suspended in PBST containing phycoerythrin-labelled antibody reagent (25 μL), and incubated for 20 minutes at 37 degrees Celsius.

After washing four times with PBST (100 μL each), the beads were resuspended in PBST and processed through a Luminex flow cytometry detector to interrogate the beads for binding of the individual hemoglobin species present in the samples. For example, samples from homozygous hemoglobin AA individuals exhibited signal from the HbA1c and HbA0 beads, and samples from heterozygous hemoglobin variant individuals exhibited signal from the $HbA_0$, $HbA_{1c}$ and the specific hemoglobin variant beads. The phycoerythrin-derived fluorescent signal of each bead was measured for the samples and calibrators. A calibration curve was constructed for each hemoglobin analyte using the signal from the bead and the known dose of the respective calibrators. The concentration of the hemoglobin analytes in each sample was determined from their fluorescent signal and the established dose-response of the calibration curve. Percent $HbA_{1c}$ and percent hemoglobin variant, if any, in the samples were determined by dividing the concentration of hemoglobin $A_{1c}$ or variant hemoglobin protein by the concentration of $HbA_0$, each derived from their respective bead. In the case of heterozygous hemoglobin variant-containing samples (such as HbAS, for example), the percent $A_{1c}$ value derived from the ratio of the $A_{1c}$ to $HbA_0$ concentrations was adjusted when needed using the concentration of the hemoglobin variant present in the sample, to provide a value that best reflected the true glycemic index of the individual.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety for their disclosures of the subject matter in whose connection they are cited herein. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A monoclonal antibody that selectively binds to hemoglobin variant HbD and glycated HbD, wherein the antibody binds to a HbD minimal epitope $^{121}$QMP$^{125}$ (SEQ ID NO:8) or $^{119}$GKQFTPP$^{125}$ (SEQ ID NO:46); and is raised against an HbD immunogen: H2N-CYG-VLAHHFGKQFTP-PVQAA-CONH2 (SEQ ID NO:32) or H2N-QFTP-PVQAAYQKVVAGV-GYC-CONH2 (SEQ ID NO:33).

2. A monoclonal antibody that selectively binds to hemoglobin variant HbE and glycated HbE, wherein the antibody binds to a HbE minimal epitope $^{22}$EVGGK$^{26}$ (SEQ ID NO:6) or $^{21}$DEVGGK$^{26}$ (SEQ ID NO:7); and is raised against an HbE immunogen consisting of H2N-CYG-VTALWGKVNVDEVGGK-CONH2 (SEQ ID NO:29).

3. A monoclonal antibody that selectively binds to hemoglobin variant HbE and glycated HbE, wherein the monoclonal antibody selectively binds an HbE immunogen consisting of H2N-CYG-VTALWGKVNVDEVGGK-CONH2 (SEQ ID NO:29).

* * * * *

UNITED STATES PATENT AND TRADEMARK OFFICE

CERTIFICATE OF CORRECTION

PATENT NO. : 9,605,060 B2
APPLICATION NO. : 14/947939
DATED : March 28, 2017
INVENTOR(S) : Roger Walker et al.

It is certified that error appears in the above-identified patent and that said Letters Patent is hereby corrected as shown below:

In the Claims

Column 43, Line 3 Claim 1: delete "$^{121}$QMP$^{125}$" and insert --$^{121}$QFTPP$^{125}$--.

Signed and Sealed this
Twelfth Day of September, 2017

Joseph Matal

*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 46

<210> SEQ ID NO 1
<211> LENGTH: 9
<212> TYPE: PRT
<213> ORGANISM: Artificial Sequence
<220> FEATURE:
<223> OTHER INFORMATION: synthetic anti-hemoglobin variant HbC
      monoclonal antibody minimal epitope

<400> SEQUENCE: 1

Thr Pro Lys Glu Lys Ser Ala Val Thr
 1               5


<210> SEQ ID NO 2
<211> LENGTH: 5
<212> TYPE: PRT
<213> ORGANISM: Artificial Sequence
<220> FEATURE:
<223> OTHER INFORMATION: synthetic anti-hemoglobin variant HbC
      monoclonal antibody minimal epitope
<220> FEATURE:
<221> NAME/KEY: VARIANT
<222> LOCATION: (3)...(3)
<223> OTHER INFORMATION: Xaa = any naturally occurring amino acid

<400> SEQUENCE: 2

Leu Thr Xaa Lys Glu
 1               5


<210> SEQ ID NO 3
<211> LENGTH: 10
<212> TYPE: PRT
<213> ORGANISM: Artificial Sequence
<220> FEATURE:
<223> OTHER INFORMATION: synthetic anti-hemoglobin variant HbS
      monoclonal antibody minimal epitope

<400> SEQUENCE: 3

Leu Thr Pro Val Glu Lys Ser Ala Val Thr
 1               5                  10


<210> SEQ ID NO 4
<211> LENGTH: 6
<212> TYPE: PRT
<213> ORGANISM: Artificial Sequence
<220> FEATURE:
<223> OTHER INFORMATION: synthetic anti-hemoglobin variant HbS
      monoclonal antibody minimal epitope
<220> FEATURE:
<221> NAME/KEY: VARIANT
<222> LOCATION: (4)...(5)
<223> OTHER INFORMATION: Xaa = any naturally occurring amino acid

<400> SEQUENCE: 4
```

-continued

Pro Val Glu Xaa Xaa Ala
1 5

<210> SEQ ID NO 5
<211> LENGTH: 8
<212> TYPE: PRT
<213> ORGANISM: Artificial Sequence
<220> FEATURE:
<223> OTHER INFORMATION: synthetic anti-hemoglobin variant HbC
monoclonal antibody minimal epitope
<220> FEATURE:
<221> NAME/KEY: VARIANT
<222> LOCATION: (6)...(7)
<223> OTHER INFORMATION: Xaa = any naturally occurring amino acid

<400> SEQUENCE: 5

Leu Thr Pro Val Glu Xaa Xaa Ala
1 5

<210> SEQ ID NO 6
<211> LENGTH: 5
<212> TYPE: PRT
<213> ORGANISM: Artificial Sequence
<220> FEATURE:
<223> OTHER INFORMATION: synthetic anti-hemoglobin variant HbE
monoclonal antibody minimal epitope

<400> SEQUENCE: 6

Glu Val Gly Gly Lys
1 5

<210> SEQ ID NO 7
<211> LENGTH: 6
<212> TYPE: PRT
<213> ORGANISM: Artificial Sequence
<220> FEATURE:
<223> OTHER INFORMATION: synthetic anti-hemoglobin variant HbE
monoclonal antibody minimal epitope

<400> SEQUENCE: 7

Asp Glu Val Gly Gly Lys
1 5

<210> SEQ ID NO 8
<211> LENGTH: 5
<212> TYPE: PRT
<213> ORGANISM: Artificial Sequence
<220> FEATURE:
<223> OTHER INFORMATION: synthetic anti-hemoglobin variant HbD
monoclonal antibody minimal epitope

<400> SEQUENCE: 8

Gln Phe Thr Pro Pro
1 5

<210> SEQ ID NO 9
<211> LENGTH: 7
<212> TYPE: PRT
<213> ORGANISM: Artificial Sequence
<220> FEATURE:
<223> OTHER INFORMATION: synthetic anti-hemoglobin variant HbD
monoclonal antibody minimal epitope
<220> FEATURE:
<221> NAME/KEY: VARIANT
<222> LOCATION: (2)...(5)
<223> OTHER INFORMATION: Xaa = any naturally occurring amino acid

<400> SEQUENCE: 9

```
Gly Xaa Gln Phe Xaa Pro Pro
 1              5


<210> SEQ ID NO 10
<211> LENGTH: 5
<212> TYPE: PRT
<213> ORGANISM: Artificial Sequence
<220> FEATURE:
<223> OTHER INFORMATION: synthetic anti-hemoglobin variant HbD
      monoclonal antibody minimal epitope
<220> FEATURE:
<221> NAME/KEY: VARIANT
<222> LOCATION: (3)...(3)
<223> OTHER INFORMATION: Xaa = any naturally occurring amino acid

<400> SEQUENCE: 10

Gln Phe Xaa Pro Pro
 1              5


<210> SEQ ID NO 11
<211> LENGTH: 50
<212> TYPE: PRT
<213> ORGANISM: Artificial Sequence
<220> FEATURE:
<223> OTHER INFORMATION: synthetic pan-reactive anti-alpha globin
      polyclonal antibody epitope

<400> SEQUENCE: 11

Ser His Gly Ser Ala Gln Val Lys Gly His Gly Lys Lys Val Ala Asp
 1              5                   10                  15

Ala Leu Thr Asn Ala Val Ala His Val Asp Asp Met Pro Asn Ala Leu
            20                  25                  30

Ser Ala Leu Ser Asp His Leu His Ala His Lys Leu Arg Arg Val Asp
        35                  40                  45

Pro Val
    50


<210> SEQ ID NO 12
<211> LENGTH: 15
<212> TYPE: PRT
<213> ORGANISM: Artificial Sequence
<220> FEATURE:
<223> OTHER INFORMATION: synthetic pan-reactive anti-beta globin
      polyclonal antibody epitope

<400> SEQUENCE: 12

Trp Gly Lys Val Asn Val Asp Glu Val Gly Gly Glu Ala Leu Gly
 1              5                   10                  15


<210> SEQ ID NO 13
<211> LENGTH: 7
<212> TYPE: PRT
<213> ORGANISM: Artificial Sequence
<220> FEATURE:
<223> OTHER INFORMATION: synthetic pan-reactive anti-beta globin
      polyclonal antibody epitope

<400> SEQUENCE: 13

Phe Gly Asp Leu Ser Thr Pro
 1              5


<210> SEQ ID NO 14
<211> LENGTH: 12
<212> TYPE: PRT
<213> ORGANISM: Artificial Sequence
<220> FEATURE:
<223> OTHER INFORMATION: synthetic pan-reactive anti-beta globin
```

polyclonal antibody epitope

<400> SEQUENCE: 14

Ala His Leu Asp Asn Leu Lys Gly Thr Phe Ala Thr
1 5 10

<210> SEQ ID NO 15
<211> LENGTH: 12
<212> TYPE: PRT
<213> ORGANISM: Artificial Sequence
<220> FEATURE:
<223> OTHER INFORMATION: synthetic pan-reactive anti-beta globin polyclonal or monoclonal antibody epitope

<400> SEQUENCE: 15

Ser Ala Val Thr Ala Leu Trp Gly Lys Val Asn Val
1 5 10

<210> SEQ ID NO 16
<211> LENGTH: 13
<212> TYPE: PRT
<213> ORGANISM: Artificial Sequence
<220> FEATURE:
<223> OTHER INFORMATION: synthetic pan-reactive anti-beta globin polyclonal or monoclonal antibody epitope, anti-beta globin antibody epitope

<400> SEQUENCE: 16

Lys Ser Ala Val Thr Ala Leu Trp Gly Lys Val Asn Val
1 5 10

<210> SEQ ID NO 17
<211> LENGTH: 5
<212> TYPE: PRT
<213> ORGANISM: Artificial Sequence
<220> FEATURE:
<223> OTHER INFORMATION: synthetic pan-reactive anti-beta globin polyclonal or monoclonal antibody epitope

<400> SEQUENCE: 17

Val Thr Ala Leu Trp
1 5

<210> SEQ ID NO 18
<211> LENGTH: 4
<212> TYPE: PRT
<213> ORGANISM: Artificial Sequence
<220> FEATURE:
<223> OTHER INFORMATION: synthetic pan-reactive anti-beta globin polyclonal or monoclonal antibody minimal epitope

<400> SEQUENCE: 18

Ala Leu Trp Gly
1

<210> SEQ ID NO 19
<211> LENGTH: 5
<212> TYPE: PRT
<213> ORGANISM: Artificial Sequence
<220> FEATURE:
<223> OTHER INFORMATION: synthetic pan-reactive anti-beta globin polyclonal or monoclonal antibody minimal epitope
<220> FEATURE:
<221> NAME/KEY: VARIANT
<222> LOCATION: (3)...(3)
<223> OTHER INFORMATION: Xaa = any naturally occurring amino acid

<400> SEQUENCE: 19

Val Thr Xaa Leu Trp
1 5

<210> SEQ ID NO 20
<211> LENGTH: 14
<212> TYPE: PRT
<213> ORGANISM: Artificial Sequence
<220> FEATURE:
<223> OTHER INFORMATION: synthetic anti-beta globin antibody epitope

<400> SEQUENCE: 20

Pro Lys Val Lys Ala His Gly Lys Lys Val Leu Gly Ala Phe
1 5 10

<210> SEQ ID NO 21
<211> LENGTH: 18
<212> TYPE: PRT
<213> ORGANISM: Artificial Sequence
<220> FEATURE:
<223> OTHER INFORMATION: synthetic anti-beta globin antibody epitope

<400> SEQUENCE: 21

Thr Leu Ser Glu Leu His Cys Asp Lys Leu His Val Asp Pro Glu Asn
1 5 10 15

Phe Arg

<210> SEQ ID NO 22
<211> LENGTH: 146
<212> TYPE: PRT
<213> ORGANISM: Homo sapiens
<220> FEATURE:
<223> OTHER INFORMATION: human hemoglobin beta chain, beta globin chain

<400> SEQUENCE: 22

Val His Leu Thr Pro Glu Glu Lys Ser Ala Val Thr Ala Leu Trp Gly
1 5 10 15

Lys Val Asn Val Asp Glu Val Gly Gly Glu Ala Leu Gly Arg Leu Leu
20 25 30

Val Val Tyr Pro Trp Thr Gln Arg Phe Phe Glu Ser Phe Gly Asp Leu
35 40 45

Ser Thr Pro Asp Ala Val Met Gly Asn Pro Lys Val Lys Ala His Gly
50 55 60

Lys Lys Val Leu Gly Ala Phe Ser Asp Gly Leu Ala His Leu Asp Asn
65 70 75 80

Leu Lys Gly Thr Phe Ala Thr Leu Ser Glu Leu His Cys Asp Lys Leu
85 90 95

His Val Asp Pro Glu Asn Phe Arg Leu Leu Gly Asn Val Leu Val Cys
100 105 110

Val Leu Ala His His Phe Gly Lys Glu Phe Thr Pro Pro Val Gln Ala
115 120 125

Ala Tyr Gln Lys Val Val Ala Gly Val Ala Asn Ala Leu Ala His Lys
130 135 140

Tyr His
145

<210> SEQ ID NO 23
<211> LENGTH: 16
<212> TYPE: PRT
<213> ORGANISM: Artificial Sequence
<220> FEATURE:
<223> OTHER INFORMATION: synthetic hemoglobin H1 peptide
<220> FEATURE:

-continued

```
<221> NAME/KEY: AMIDATION
<222> LOCATION: (16)...(16)
<223> OTHER INFORMATION: cysteinamide

<400> SEQUENCE: 23

Val His Leu Thr Pro Glu Glu Lys Ser Ala Val Thr Ala Leu Trp Cys
 1               5                   10                  15


<210> SEQ ID NO 24
<211> LENGTH: 16
<212> TYPE: PRT
<213> ORGANISM: Artificial Sequence
<220> FEATURE:
<223> OTHER INFORMATION: synthetic hemoglobin H2 peptide
<220> FEATURE:
<221> NAME/KEY: AMIDATION
<222> LOCATION: (16)...(16)
<223> OTHER INFORMATION: cysteinamide

<400> SEQUENCE: 24

Val His Leu Thr Pro Glu Glu Ala Ser Ala Ser Thr Ala Ser Trp Cys
 1               5                   10                  15


<210> SEQ ID NO 25
<211> LENGTH: 16
<212> TYPE: PRT
<213> ORGANISM: Artificial Sequence
<220> FEATURE:
<223> OTHER INFORMATION: synthetic hemoglobin H2bis peptide
<220> FEATURE:
<221> NAME/KEY: AMIDATION
<222> LOCATION: (16)...(16)
<223> OTHER INFORMATION: cysteinamide

<400> SEQUENCE: 25

Val His Leu Thr Pro Glu Glu Lys Ser Ala Ser Thr Ala Ser Trp Cys
 1               5                   10                  15


<210> SEQ ID NO 26
<211> LENGTH: 16
<212> TYPE: PRT
<213> ORGANISM: Artificial Sequence
<220> FEATURE:
<223> OTHER INFORMATION: synthetic hemoglobin variant HbS H3 peptide
<220> FEATURE:
<221> NAME/KEY: AMIDATION
<222> LOCATION: (16)...(16)
<223> OTHER INFORMATION: cysteinamide

<400> SEQUENCE: 26

Val His Leu Thr Pro Val Glu Lys Ser Ala Val Thr Ala Leu Trp Cys
 1               5                   10                  15


<210> SEQ ID NO 27
<211> LENGTH: 16
<212> TYPE: PRT
<213> ORGANISM: Artificial Sequence
<220> FEATURE:
<223> OTHER INFORMATION: synthetic hemoglobin variant HbC H4 peptide
<220> FEATURE:
<221> NAME/KEY: AMIDATION
<222> LOCATION: (16)...(16)
<223> OTHER INFORMATION: cysteinamide

<400> SEQUENCE: 27

Val His Leu Thr Pro Lys Glu Lys Ser Ala Val Thr Ala Leu Trp Cys
 1               5                   10                  15


<210> SEQ ID NO 28
```

-continued

<211> LENGTH: 15
<212> TYPE: PRT
<213> ORGANISM: Artificial Sequence
<220> FEATURE:
<223> OTHER INFORMATION: synthetic hemoglobin variant HbE H5 peptide
<220> FEATURE:
<221> NAME/KEY: MOD_RES
<222> LOCATION: (1)...(1)
<223> OTHER INFORMATION: Asn modified by CYG
<220> FEATURE:
<221> NAME/KEY: AMIDATION
<222> LOCATION: (15)...(15)
<223> OTHER INFORMATION: valinamide

<400> SEQUENCE: 28

Asn Val Asp Glu Val Gly Gly Lys Ala Leu Gly Arg Leu Leu Val
1 5 10 15

<210> SEQ ID NO 29
<211> LENGTH: 16
<212> TYPE: PRT
<213> ORGANISM: Artificial Sequence
<220> FEATURE:
<223> OTHER INFORMATION: synthetic hemoglobin variant HbE H5bis peptide
<220> FEATURE:
<221> NAME/KEY: MOD_RES
<222> LOCATION: (1)...(1)
<223> OTHER INFORMATION: Val modified by CYG
<220> FEATURE:
<221> NAME/KEY: AMIDATION
<222> LOCATION: (16)...(16)
<223> OTHER INFORMATION: lysinamide

<400> SEQUENCE: 29

Val Thr Ala Leu Trp Gly Lys Val Asn Val Asp Glu Val Gly Gly Lys
1 5 10 15

<210> SEQ ID NO 30
<211> LENGTH: 10
<212> TYPE: PRT
<213> ORGANISM: Artificial Sequence
<220> FEATURE:
<223> OTHER INFORMATION: synthetic hemoglobin variant HbE H10 peptide
<220> FEATURE:
<221> NAME/KEY: MOD_RES
<222> LOCATION: (2)...(2)
<223> OTHER INFORMATION: Xaa = 6-amino hexanoic acid
<220> FEATURE:
<221> NAME/KEY: AMIDATION
<222> LOCATION: (10)...(10)
<223> OTHER INFORMATION: glycinamide

<400> SEQUENCE: 30

Cys Xaa Glu Val Gly Gly Lys Ala Leu Gly
1 5 10

<210> SEQ ID NO 31
<211> LENGTH: 10
<212> TYPE: PRT
<213> ORGANISM: Artificial Sequence
<220> FEATURE:
<223> OTHER INFORMATION: synthetic hemoglobin variant HbE H10bis peptide
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: AMIDATION
<222> LOCATION: (10)...(10)
<223> OTHER INFORMATION: cysteinamide

<400> SEQUENCE: 31

Glu Val Gly Gly Lys Ala Leu Gly Xaa Cys
1 5 10

<210> SEQ ID NO 32
<211> LENGTH: 17
<212> TYPE: PRT
<213> ORGANISM: Artificial Sequence
<220> FEATURE:
<223> OTHER INFORMATION: synthetic hemoglobin variant HbD H6 peptide
<220> FEATURE:
<221> NAME/KEY: MOD_RES
<222> LOCATION: (1)...(1)
<223> OTHER INFORMATION: Val modified by CYG
<220> FEATURE:
<221> NAME/KEY: AMIDATION
<222> LOCATION: (17)...(17)
<223> OTHER INFORMATION: alaninamide

<400> SEQUENCE: 32

Val Leu Ala His His Phe Gly Lys Gln Phe Thr Pro Pro Val Gln Ala
1 5 10 15

Ala

<210> SEQ ID NO 33
<211> LENGTH: 17
<212> TYPE: PRT
<213> ORGANISM: Artificial Sequence
<220> FEATURE:
<223> OTHER INFORMATION: synthetic hemoglobin variant HbD H6bis peptide
<220> FEATURE:
<221> NAME/KEY: MOD_RES
<222> LOCATION: (17)...(17)
<223> OTHER INFORMATION: valinamide modified by GYC

<400> SEQUENCE: 33

Gln Phe Thr Pro Pro Val Gln Ala Ala Tyr Gln Lys Val Val Ala Gly
1 5 10 15

Val

<210> SEQ ID NO 34
<211> LENGTH: 15
<212> TYPE: PRT
<213> ORGANISM: Artificial Sequence
<220> FEATURE:
<223> OTHER INFORMATION: synthetic hemoglobin variant HbD H9 peptide
<220> FEATURE:
<221> NAME/KEY: MOD_RES
<222> LOCATION: (15)...(15)
<223> OTHER INFORMATION: threoninamide modified by GYC

<400> SEQUENCE: 34

Gly Lys Gln Phe Thr Gly Lys Gln Phe Thr Gly Lys Gln Phe Thr
1 5 10 15

<210> SEQ ID NO 35
<211> LENGTH: 10
<212> TYPE: PRT
<213> ORGANISM: Artificial Sequence
<220> FEATURE:
<223> OTHER INFORMATION: synthetic hemoglobin variant HbD H11 peptide
<220> FEATURE:
<221> NAME/KEY: MOD_RES
<222> LOCATION: (2)...(2)
<223> OTHER INFORMATION: Xaa = 6-amino hexanoic acid
<220> FEATURE:
<221> NAME/KEY: AMIDATION
<222> LOCATION: (10)...(10)
<223> OTHER INFORMATION: prolinamide

<400> SEQUENCE: 35

```
Cys Xaa His Phe Gly Lys Gln Phe Thr Pro
 1               5                  10


<210> SEQ ID NO 36
<211> LENGTH: 10
<212> TYPE: PRT
<213> ORGANISM: Artificial Sequence
<220> FEATURE:
<223> OTHER INFORMATION: synthetic hemoglobin variant HbD H11bis
      peptide
<220> FEATURE:
<221> NAME/KEY: MOD_RES
<222> LOCATION: (9)...(9)
<223> OTHER INFORMATION: Xaa = 6-amoino hexanoic acid
<220> FEATURE:
<221> NAME/KEY: AMIDATION
<222> LOCATION: (10)...(10)
<223> OTHER INFORMATION: cysteinamide

<400> SEQUENCE: 36

His Phe Gly Lys Gln Phe Thr Pro Xaa Cys
 1               5                  10


<210> SEQ ID NO 37
<211> LENGTH: 9
<212> TYPE: PRT
<213> ORGANISM: Artificial Sequence
<220> FEATURE:
<223> OTHER INFORMATION: synthetic hemoglobin variant HbA1-c GP1 peptide
<220> FEATURE:
<221> NAME/KEY: MOD_RES
<222> LOCATION: (1)...(1)
<223> OTHER INFORMATION: Val modified by glucose
<220> FEATURE:
<221> NAME/KEY: MOD_RES
<222> LOCATION: (8)...(8)
<223> OTHER INFORMATION: Xaa = 6-amino hexanoic acid
<220> FEATURE:
<221> NAME/KEY: AMIDATION
<222> LOCATION: (9)...(9)
<223> OTHER INFORMATION: cysteinamide

<400> SEQUENCE: 37

Val His Leu Thr Pro Glu Glu Xaa Cys
 1               5


<210> SEQ ID NO 38
<211> LENGTH: 9
<212> TYPE: PRT
<213> ORGANISM: Artificial Sequence
<220> FEATURE:
<223> OTHER INFORMATION: synthetic hemoglobin variant HbA1-c GP3 peptide
<220> FEATURE:
<221> NAME/KEY: MOD_RES
<222> LOCATION: (1)...(1)
<223> OTHER INFORMATION: Val modified by 1-deoxy-fructopyranosyl group
<220> FEATURE:
<221> NAME/KEY: MOD_RES
<222> LOCATION: (8)...(8)
<223> OTHER INFORMATION: Xaa = 6-amino hexanoic acid
<220> FEATURE:
<221> NAME/KEY: AMIDATION
<222> LOCATION: (9)...(9)
<223> OTHER INFORMATION: cysteinamide

<400> SEQUENCE: 38

Val His Leu Thr Pro Glu Glu Xaa Cys
 1               5


<210> SEQ ID NO 39
<211> LENGTH: 16
```

```
<212> TYPE: PRT
<213> ORGANISM: Artificial Sequence
<220> FEATURE:
<223> OTHER INFORMATION: synthetic hemoglobin variant HbA1-c glycated H2
      peptide
<220> FEATURE:
<221> NAME/KEY: MOD_RES
<222> LOCATION: (1)...(1)
<223> OTHER INFORMATION: Val modified by glucose
<220> FEATURE:
<221> NAME/KEY: AMIDATION
<222> LOCATION: (16)...(16)
<223> OTHER INFORMATION: cysteinamide

<400> SEQUENCE: 39

Val His Leu Thr Pro Glu Glu Ala Ser Ala Ser Thr Ala Ser Trp Cys
 1               5                  10                  15


<210> SEQ ID NO 40
<211> LENGTH: 8
<212> TYPE: PRT
<213> ORGANISM: Artificial Sequence
<220> FEATURE:
<223> OTHER INFORMATION: synthetic anti-hemoglobin variant HbS antibody
      minimal epitope

<400> SEQUENCE: 40

Pro Val Glu Lys Ser Ala Val Thr
 1               5


<210> SEQ ID NO 41
<211> LENGTH: 7
<212> TYPE: PRT
<213> ORGANISM: Artificial Sequence
<220> FEATURE:
<223> OTHER INFORMATION: synthetic anti-hemoglobin variant HbS antibody
      minimal epitope residues important for binding

<400> SEQUENCE: 41

His Leu Thr Pro Val Glu Lys
 1               5


<210> SEQ ID NO 42
<211> LENGTH: 14
<212> TYPE: PRT
<213> ORGANISM: Artificial Sequence
<220> FEATURE:
<223> OTHER INFORMATION: synthetic pan-reactive anti-beta globin
      polyclonal antibody epitope

<400> SEQUENCE: 42

Gly Lys Val Asn Val Asp Glu Val Gly Gly Glu Ala Leu Gly
 1               5                  10


<210> SEQ ID NO 43
<211> LENGTH: 6
<212> TYPE: PRT
<213> ORGANISM: Artificial Sequence
<220> FEATURE:
<223> OTHER INFORMATION: synthetic pan-reactive anti-beta globin
      polyclonal antibody epitope

<400> SEQUENCE: 43

Gly Asp Leu Ser Thr Pro
 1               5


<210> SEQ ID NO 44
<211> LENGTH: 10
<212> TYPE: PRT
```

-continued

```
<213> ORGANISM: Artificial Sequence
<220> FEATURE:
<223> OTHER INFORMATION: synthetic pan-reactive anti-beta globin
      polyclonal antibody epitope

<400> SEQUENCE: 44

Leu Asp Asn Leu Lys Gly Thr Phe Ala Thr
 1               5                   10


<210> SEQ ID NO 45
<211> LENGTH: 7
<212> TYPE: PRT
<213> ORGANISM: Artificial Sequence
<220> FEATURE:
<223> OTHER INFORMATION: synthetic hemoglobin variant HbA1-c
      unglycated RW1a peptide
<220> FEATURE:
<221> NAME/KEY: AMIDATION
<222> LOCATION: (7)...(7)
<223> OTHER INFORMATION: glutamic acid amide

<400> SEQUENCE: 45

Val His Leu Thr Pro Glu Glu
 1               5


<210> SEQ ID NO 46
<211> LENGTH: 7
<212> TYPE: PRT
<213> ORGANISM: Artificial Sequence
<220> FEATURE:
<223> OTHER INFORMATION: synthetic anti-hemoglobin variant HbD
      monoclonal antibody minimal epitope

<400> SEQUENCE: 46

Gly Lys Gln Phe Thr Pro Pro
 1               5
```